US011562323B2

(12) United States Patent
Eberhardt, III et al.

(10) Patent No.: US 11,562,323 B2
(45) Date of Patent: Jan. 24, 2023

(54) APPLICATION OF BAYESIAN NETWORKS TO PATIENT SCREENING AND TREATMENT

(75) Inventors: John S. Eberhardt, III, Jeffersonton, VA (US); Philip M. Kalina, Reston, VA (US); Todd A. Radano, Jeffersonton, VA (US)

(73) Assignee: DECISIONQ CORPORATION, Washington, DC (US)

( * ) Notice: Subject to any disclaimer, the term of this patent is extended or adjusted under 35 U.S.C. 154(b) by 51 days.

(21) Appl. No.: 12/895,598

(22) Filed: Sep. 30, 2010

(65) Prior Publication Data
US 2011/0082712 A1  Apr. 7, 2011

Related U.S. Application Data

(60) Provisional application No. 61/247,937, filed on Oct. 1, 2009.

(51) Int. Cl.
*G06Q 40/00* (2012.01)
*G06Q 10/10* (2012.01)
(Continued)

(52) U.S. Cl.
CPC .............. *G06Q 10/10* (2013.01); *G06Q 40/08* (2013.01); *G16H 50/20* (2018.01); *G16H 50/50* (2018.01); *G16Z 99/00* (2019.02)

(58) Field of Classification Search
CPC ........ G06Q 50/22; G06Q 40/08; G06Q 50/24; G06Q 10/10; G06F 19/345; G06F 19/3437; G06F 19/00; G16H 50/50; G16H 50/20

USPC ............... 341/118; 382/187; 434/118; 435/6; 600/300, 587; 607/58; 702/19; 703/11; 704/254; 705/4, 36 R, 2, 3; 706/12, 45, 706/46
See application file for complete search history.

(56) References Cited

U.S. PATENT DOCUMENTS 7,003,158 B1 * 2/2006 Bennett et al. ............... 382/187
7,392,201 B1 * 6/2008 Binns et al. ..................... 705/4
(Continued)

OTHER PUBLICATIONS

•Ref. U—Robert A. van Engelen, Approximating Bayesian Belief networks by Arc Removal, IEEE Transactions on Pattern Analysis and Machine Intelligence, vol. 19, No. 8, Aug. 1997.*
(Continued)

*Primary Examiner* — Rajesh Khattar
(74) *Attorney, Agent, or Firm* — ArentFox Schiff LLP

(57) ABSTRACT

According to one aspect of the invention, health insurance claim data for a first group of individuals is obtained to generate a training corpus, including a training set of claim data and a holdout set of claim data. The first group of individuals represents enrollees of one or more first health insurance plans and the health insurance claim data represents historic insurance claim information for each individual in the first group. A Bayesian belief network (BBN) model is created by training a BBN network based on the training set of claim data using predetermined machine learning algorithms. The BBN model is validated using the holdout set of claim data. The BBN model, when having been successfully validated, is configured to identify at least one of individuals with risk for a disorder and individuals with risk who are most likely to benefit from intervention and treatment for the disorder.

20 Claims, 23 Drawing Sheets

(51) Int. Cl.
*G06Q 40/08* (2012.01)
*G16H 50/50* (2018.01)
*G16H 50/20* (2018.01)
*G16Z 99/00* (2019.01)

(56) References Cited

U.S. PATENT DOCUMENTS

| | | | |
|---|---|---|---|
| 7,739,126 B1* | 6/2010 | Cave et al. | 705/2 |
| 7,813,944 B1* | 10/2010 | Luk et al. | 705/4 |
| 2002/0087344 A1* | 7/2002 | Billings et al. | 705/1 |
| 2003/0130973 A1* | 7/2003 | Sumner et al. | 706/45 |
| 2004/0059608 A1* | 3/2004 | Gore et al. | 705/4 |
| 2005/0060008 A1* | 3/2005 | Goetz | 607/48 |
| 2005/0080462 A1* | 4/2005 | Jenkins et al. | 607/58 |
| 2005/0118557 A1* | 6/2005 | Sumner et al. | 434/118 |
| 2005/0131848 A1* | 6/2005 | Chickering et al. | 706/12 |
| 2005/0165285 A1* | 7/2005 | Iliff | 600/300 |
| 2005/0240447 A1* | 10/2005 | Kil et al. | 705/4 |
| 2005/0289092 A1* | 12/2005 | Sumner et al. | 706/46 |
| 2006/0089862 A1* | 4/2006 | Anandarao et al. | 705/4 |
| 2006/0173715 A1* | 8/2006 | Wang | 705/2 |
| 2007/0050288 A1* | 3/2007 | Sarkar et al. | 705/38 |
| 2007/0112597 A1* | 5/2007 | Heckerman et al. | 705/2 |
| 2008/0103903 A1* | 5/2008 | Flake et al. | 705/14 |
| 2008/0120108 A1* | 5/2008 | Soong et al. | 704/254 |
| 2008/0168015 A1* | 7/2008 | Thie et al. | 706/46 |
| 2008/0174460 A1* | 7/2008 | Vigoda | 341/118 |
| 2008/0294565 A1* | 11/2008 | Kongtcheu | |
| 2009/0048877 A1* | 2/2009 | Binns et al. | 705/4 |
| 2009/0055150 A1* | 2/2009 | Prior et al. | 703/11 |
| 2009/0061422 A1* | 3/2009 | Linke et al. | 435/6 |
| 2009/0070279 A1* | 3/2009 | Rajabally | 706/12 |
| 2009/0150190 A1* | 6/2009 | Solomon et al. | 705/4 |
| 2009/0198733 A1* | 8/2009 | Gounares et al. | 707/104.1 |
| 2009/0254328 A1* | 10/2009 | Chbat et al. | 703/11 |
| 2009/0271124 A1* | 10/2009 | Urdea et al. | 702/19 |
| 2010/0004956 A1* | 1/2010 | Mccallum et al. | 705/4 |
| 2010/0131307 A1* | 5/2010 | Collopy et al. | 705/4 |
| 2010/0168621 A1* | 7/2010 | Neville | 600/587 |
| 2010/0293000 A1* | 11/2010 | Hu et al. | 705/2 |
| 2011/0112380 A1* | 5/2011 | Robinson | A61B 5/0002 600/300 |
| 2011/0289035 A1* | 11/2011 | Stojadinovic et al. | 706/45 |
| 2012/0004893 A1* | 1/2012 | Vaidyanathan et al. | 703/11 |
| 2012/0123232 A1* | 5/2012 | Najarian et al. | 600/345 |
| 2012/0245439 A1* | 9/2012 | Andre et al. | 600/310 |
| 2016/0360980 A1* | 12/2016 | Sinha | A61B 5/4857 |

OTHER PUBLICATIONS

•Ref V—Changyun Wang, Bayesian Belief Network Simulation, Department of computer Science, Florida State University, Feb. 24, 2003.*
• Robert A. van Engelen, Approximating Bayesian Belief networks by Arc Removal, IEEE Transactions on Pattern Analysis and Machine Intelligence, vol. 19, No. 8, Aug. 1997.*
• Ramoni et al., Learning Bayesian Networks from Incomplete Databases. Statistical Research Paper No. 13. Dept. of Actuarial Science & Statistic, City Univ., London, Jun. 1997 (25 pages).*
• Cadez et al., Empirical evaluations of some benchmark Bayesian networks. 275B Class Project. Fall Quarter, 1998 (41 pages) http://www-nt.cs.berkeley.edu/home/nir/public_html/Repository/index.htm.*
• Wang et al., Computer-assisted diagnosis of breast cancer using a data-driven Bayesian belief network. Intl Journal of Medical Informatics, 54 (1999) pp. 115-126.*
• Wooldridge, Scott, Bayesian Belief Networks, Australian Institute of Marine Science. Prepared for CSIRO Centre for Complex Systems Science. CSIRO 2003.*
• Watt et al., Evaluation of a Dynamic Bayesian Belief Network to Predict Osteoarthritic Knee Pain using Data from the Osteoarthritis Initiative. AMIA Annual Symposium Proceedings Archive, Univ. of California Los Angeles, CA. 2008.*
• Li et al., Using spatial analysis and Bayesian network to model the vulnerability and make insurance pricing of catastrophic risk. Intl Journal of Geographical Information Science. vol. 24, No. 12, Dec. 2010. pp. 1759-1784.*
• Weinstein et al., Application of Multivariate Probabilistic (Bayesian) Networks to Substance use disorder risk stratification and cost estimation. Perspect Health Inf Manag. 2009; 6(Fall): 1b. Published online Sep. 16, 2009 (27 pages).*
• Lauria et al., Misplacing the Code: An Examination of Data Quality Issues in Bayesian Text Classification for Automated Coding of Medical Diagnoses. Idea Group Inc. IRMA Intl Conference, 2007. pp. 1218-1221.*
• Cooper et al. A Bayesian Method for the Induction of Probabilistic Networks from Data. Kluwer Academic Publishers, Boston, Manufactured in The Netherlands. Machine Learning, 9, pp. 309-347 (1192).*
Weinstein, Lawrence et al., "Application Of Multivariate Probabilistic (Bayesian) Networks to Substance Use Disorder Risk Stratification and Cost Estimation," Perspectives in Health Information Management, vol. 6, Fall 2009, pp. 1-27.

* cited by examiner

| Threshold Probability of CD* | Sensitivity | Specificity | Detection per 100,000* | PPV | False Positives per True Positive | NPV |
|---|---|---|---|---|---|---|
| 4% (1.0x RR) | 100% | 85% | 4,000 | 23% | 3 | 100% |
| 8% (2.0x RR) | 100% | 88% | 4,000 | 27% | 3 | 100% |
| 12% (3.0x RR) | 100% | 90% | 4,000 | 30% | 2 | 100% |
| 16% (4.0x RR) | 100% | 91% | 4,000 | 32% | 2 | 100% |
| 20% (5.0x RR) | 100% | 91% | 4,000 | 34% | 2 | 100% |
| 50% (12.5x RR) | 100% | 94% | 3,994 | 44% | 1 | 100% |
| 75% (18.75x RR) | 99% | 96% | 3,978 | 53% | 1 | 100% |

* Assumes natural rate of 4%

FIG. 9A

| | 2005 Claim | 2006 Claim | 2005 or 2006 Claim |
|---|---|---|---|
| Sensitivity | | | |
| Subset of 50 | 11.8% | 7.2% | 7.3% |
| Subset of 100 | 22.8% | 13.7% | 14.3% |
| Subset of 250 | 47.3% | 19.0% | 29.7% |
| Subset of 500 | 86.2% | 26.8% | 54.7% |
| Positive Predictive Value | | | |
| Subset of 50 | 84.0% | 44.0% | 86.0% |
| Subset of 100 | 81.0% | 42.0% | 84.0% |
| Subset of 250 | 67.2% | 23.2% | 70.0% |
| Subset of 500 | 61.2% | 16.4% | 64.4% |

FIG. 9B

| Probability of case | Drivers | | | | Target | | | | | | |
|---|---|---|---|---|---|---|---|---|---|---|---|
| | Any Cd06 | mdc1st Out06 | Thergrp _pharm1 | Thergrp _pharm3 | 2006PaidRange | | | | | | |
| | | | | | a: up to 2500 | b: 2500 to 5000 | c: 5000 to 7500 | d: 7500 to 10... | e: 10000 to 2... | f: 25000 to 5... | g: 50000 plus |
| 0.012% | No | 7 | 08 | 08 | 20.4 | 15.8 | 10.6 | 9.7 | 27.3 | 11.7 | 4.6 |

FIG. 11A

| Probability of case | Drivers | | | | Target | | | | | | |
|---|---|---|---|---|---|---|---|---|---|---|---|
| | Any Cd06 | mdc1st Out06 | Thergrp _pharm1 | Thergrp _pharm3 | 2006PaidRange | | | | | | |
| | | | | | a: up to 2500 | b: 2500 to 5000 | c: 5000 to 7500 | d: 7500 to 10... | e: 10000 to 2... | f: 25000 to 5... | g: 50000 plus |
| 0.0% | Yes | 7 | 08 | 08 | 3.3 | 7.0 | 6.9 | 9.4 | 36.8 | 25.0 | 11.5 |

FIG. 11B

| Probability of case | Driver thergrp_pharm1 | Target anyCdAnyYear No | Target anyCdAnyYear Yes | Relative Risk |
|---|---|---|---|---|
| 0.00% | 14 | 66.7% | 33.3% | 8.2x |
| 0.00% | 22 | 66.7% | 33.3% | 8.2x |
| 0.00% | 19 | 83.3% | 16.7% | 4.1x |
| 0.01% | 9 | 90.0% | 10.0% | 2.5x |
| 0.05% | 21 | 91.9% | 8.1% | 2.0x |
| 0.03% | 23 | 91.9% | 8.1% | 2.0x |
| 19.23% | 8 | 93.1% | 6.9% | 1.7x |
| 0.01% | 25 | 94.1% | 5.9% | 1.5x |
| 3.60% | 17 | 95.0% | 5.0% | 1.2x |
| 2.57% | 29 | 95.0% | 5.0% | 1.2x |

FIG. 12

| Probability of case | Driver mdc1stInp04 | Target admtyp_inp1 | | | | | | Relative Risk |
|---|---|---|---|---|---|---|---|---|
| | | 1 | 2 | 3 | 4 | 5 | MISSING | |
| 0.17% | 19 | 0.4 | 0.4 | 0.3 | 97.3 | 0.3 | 1.4 | 162.2x |
| 0.08% | 20 | 1.5 | 0.8 | 0.6 | 93.5 | 0.7 | 2.9 | 155.8x |
| 0.00% | 15 | 13.7 | 14.1 | 32.6 | 14 | 12.4 | 13.2 | 23.3x |
| 0.01% | 22 | 8.4 | 60.6 | 6.7 | 8.6 | 7.6 | 8.1 | 14.3x |
| 0.01% | 2 | 15.5 | 55.9 | 6.2 | 7.9 | 7 | 7.5 | 13.2x |
| 0.01% | 25 | 7.2 | 66.4 | 5.7 | 7.3 | 6.5 | 6.9 | 12.2x |
| 0.02% | 24 | 47.1 | 43.2 | 2.1 | 2.7 | 2.4 | 2.5 | 4.5x |
| 0.03% | 17 | 35.8 | 56.4 | 1.7 | 2.2 | 1.9 | 2 | 3.7x |
| 0.03% | 16 | 11.1 | 82 | 1.5 | 1.9 | 1.7 | 1.8 | 3.2x |
| 0.03% | 23 | 44.9 | 48.2 | 1.5 | 1.9 | 1.7 | 1.8 | 3.2x |

FIG. 13

| Probability of case | Driver mdc2ndOut06 | Target 2006PaidRange | | | | | | Approx Average Paid | Approx Avg. > $7500 | Pct Over $7500 | High Cost Incidence |
|---|---|---|---|---|---|---|---|---|---|---|---|
| | | <= $2500 | $2500 to $5K | $5K to $7500 | $7500 to $10K | $10K to $25K | $25K to $50K | $50K plus | | | |
| 0.06% | HIV | 14.9 | 8.4 | 7.4 | 6.5 | 45.4 | 12.9 | 4.6 | $17,860 | $24,303 | 69.4% | 0.0% |
| 0.32% | Cancer | 35.3 | 17.5 | 12 | 6 | 11.7 | 5.8 | 11.7 | $14,943 | $37,011 | 35.2% | 0.1% |
| 0.32% | Liver/Panc | 31.3 | 16.8 | 11.2 | 7.7 | 21.1 | 7.6 | 4.2 | $12,086 | $25,378 | 40.6% | 0.1% |
| 0.34% | Pregnancy | 21.4 | 6.5 | 14.1 | 22 | 32.6 | 3 | 0.3 | $10,589 | $15,810 | 57.9% | 0.2% |
| 0.57% | Haem | 46 | 15.3 | 10.3 | 6.1 | 14.2 | 4.3 | 3.8 | $9,261 | $26,010 | 28.4% | 0.2% |
| 0.10% | CD | 45.5 | 14.4 | 8 | 8 | 18.4 | 2.9 | 2.8 | $8,766 | $22,050 | 32.1% | 0.0% |
| 2.39% | Nervous System | 39 | 19.9 | 12.9 | 7.2 | 14.4 | 4.1 | 2.5 | $8,649 | $23,169 | 28.2% | 0.7% |
| 2.07% | Kidney/ Urinary | 48.9 | 19.2 | 8.5 | 5.8 | 11.1 | 3 | 3.5 | $8,048 | $26,062 | 23.4% | 0.5% |
| 3.56% | Digestive | 41.2 | 23.3 | 11.6 | 7 | 11.9 | 3.1 | 1.9 | $7,459 | $22,033 | 23.9% | 0.9% |
| 2.94% | Respiratory | 51.3 | 18.8 | 9.3 | 5 | 10 | 3.2 | 2.4 | $7,155 | $24,932 | 20.6% | 0.6% |
| 0.52% | Drug Tox | 55 | 16.5 | 7.2 | 5.3 | 10 | 3.8 | 2.2 | $7,101 | $24,650 | 21.3% | 0.1% |
| 6.85% | Circ | 46.8 | 22.5 | 10.4 | 5.7 | 9.3 | 3.3 | 1.9 | $6,925 | $23,562 | 20.2% | 1.4% |
| 11.50% | Musc Skel | 48.9 | 19.4 | 10 | 5.8 | 11.3 | 3.3 | 1.2 | $6,690 | $21,474 | 21.6% | 2.5% |
| 2.35% | Mental | 43.1 | 21.2 | 12.6 | 6.7 | 13.1 | 2.6 | 0.7 | $6,628 | $19,158 | 23.1% | 0.5% |
| 0.04% | Burns | 59.1 | 14.8 | 6.6 | 6.5 | 8.2 | 3.3 | 1.6 | $6,228 | $22,561 | 19.6% | 0.0% |
| 0.77% | M Repro | 57.3 | 18.2 | 7.4 | 4.1 | 9.1 | 2.1 | 1.7 | $5,947 | $23,452 | 17.0% | 0.1% |
| 2.38% | F Repro | 55.9 | 16.1 | 8.6 | 5.8 | 11.1 | 1.7 | 1 | $5,791 | $19,665 | 19.6% | 0.5% |
| 8.19% | Endocrine | 47.4 | 24.4 | 11 | 5.6 | 8.6 | 2 | 1 | $5,785 | $20,353 | 17.2% | 1.4% |
| 0.36% | Infectious | 66.2 | 14.3 | 5.3 | 3.6 | 6.9 | 1.8 | 1.9 | $5,377 | $25,161 | 14.2% | 0.1% |
| 0.04% | Neonate | 69.3 | 10.8 | 3.1 | 7.7 | 6.1 | 1.5 | 1.5 | $4,972 | $20,212 | 16.8% | 0.0% |
| 6.32% | Epidermal | 62.8 | 17.2 | 7.2 | 3.9 | 6.1 | 1.6 | 1.3 | $4,946 | $22,940 | 12.9% | 0.8% |
| 2.38% | Eye | 60.5 | 17.1 | 8.1 | 4.7 | 7.3 | 1.7 | 0.7 | $4,871 | $19,886 | 14.4% | 0.3% |
| 6.49% | ENT | 62.1 | 16.7 | 7.9 | 4.1 | 7.3 | 1.3 | 0.6 | $4,591 | $19,465 | 13.3% | 0.9% |
| 16.48% | Other | 66.8 | 15.1 | 6.2 | 3.7 | 6.2 | 1.4 | 0.6 | $4,293 | $20,114 | 11.9% | 2.0% |
| 22.68% | MISSING | 98.7 | 0.9 | 0.2 | 0.1 | 0.1 | 0 | 0 | $1,455 | $13,400 | 0.2% | 0.0% |

Fig. 15A

| Probability of case | Driver mdc1stInp06 | Target 2006PaidRange | | | | | | | Approx Average Paid | Approx Avg. > $7500 | Pct Over $7500 | High Cost Incidence |
|---|---|---|---|---|---|---|---|---|---|---|---|---|
| | | <= $2500 | $2500 to $5K | $5K to $7500 | $7500 to $10K | $10K to $25K | $25K to $50K | $50K plus | | | | |
| 0.03% | Cancer | 1.9 | 1.9 | 3.7 | 1.9 | 7.5 | 18.6 | 64.6 | $54,137 | $58,105 | 92.6% | 0.0% |
| 0.02% | Trauma | 3.3 | 6.5 | 6.5 | 3.2 | 16.2 | 19.4 | 44.9 | $42,702 | $50,179 | 83.7% | 0.0% |
| 0.04% | Other | 3.4 | 5 | 3.4 | 10 | 23.5 | 23.3 | 31.4 | $36,396 | $40,753 | 88.2% | 0.0% |
| 0.07% | Infectious | 0.8 | 3.3 | 4.2 | 6.6 | 36.5 | 23.1 | 25.4 | $34,110 | $36,800 | 91.6% | 0.1% |
| 0.72% | Musculoskeletal | 0.3 | 1.2 | 2.8 | 4.7 | 35 | 38.7 | 17.5 | $33,896 | $35,109 | 95.9% | 0.7% |
| 0.88% | Circ | 0.7 | 3.3 | 5.7 | 8.2 | 31.3 | 28 | 22.9 | $33,520 | $36,533 | 90.4% | 0.8% |
| 0.29% | Nervous System | 0.2 | 2.6 | 5.3 | 7.1 | 37.6 | 23.9 | 23.3 | $33,220 | $35,674 | 91.9% | 0.3% |
| 0.04% | Haem | 5 | 1.7 | 4.9 | 6.6 | 37.9 | 18 | 26 | $32,886 | $36,659 | 88.5% | 0.0% |
| 0.07% | Drug Tox | 0.9 | 6.3 | 7.2 | 9.8 | 35 | 18.7 | 22.1 | $30,444 | $34,741 | 85.6% | 0.1% |
| 0.35% | Respiratory | 1.6 | 4 | 6.9 | 8.6 | 36.8 | 23.2 | 19 | $30,106 | $33,672 | 87.6% | 0.3% |
| 0.20% | Liver/Pancreas | 0.6 | 3.5 | 4.1 | 7.7 | 44.6 | 21.1 | 18.4 | $30,003 | $32,248 | 91.8% | 0.2% |
| 0.19% | Kidney/Urinary | 1.9 | 4.1 | 6.6 | 8.4 | 39.4 | 22.1 | 17.6 | $29,147 | $32,628 | 87.5% | 0.2% |
| 0.59% | Digestive | 1 | 2.9 | 7 | 11.8 | 41.7 | 19.2 | 16.4 | $27,886 | $30,663 | 89.1% | 0.5% |
| 0.19% | Endocrine | 0.6 | 2.8 | 6.9 | 5.3 | 46.4 | 25.9 | 12.1 | $27,680 | $30,246 | 89.7% | 0.2% |
| 0.07% | ENT | 1.8 | 5.4 | 12.5 | 9.8 | 38.5 | 12.5 | 19.5 | $27,210 | $32,618 | 80.3% | 0.1% |
| 0.16% | Epidermal | 2.3 | 7.2 | 8.3 | 10.2 | 38.1 | 16.5 | 17.5 | $27,104 | $31,927 | 82.3% | 0.1% |
| 0.01% | Burns | 10.1 | 10.1 | 10 | 10 | 20.1 | 19.9 | 19.8 | $27,075 | $37,135 | 69.8% | 0.0% |
| 0.06% | M Repro | 1 | 3 | 4 | 9 | 50.1 | 26.9 | 5.9 | $24,542 | $26,292 | 91.9% | 0.1% |
| 0.01% | HIV | 6.7 | 6.7 | 6.7 | 6.7 | 40.1 | 26.6 | 6.6 | $23,306 | $28,170 | 80.0% | 0.0% |
| 0.19% | Mental | 3.2 | 6.1 | 10.8 | 11.5 | 43.7 | 20.6 | 4.1 | $20,533 | $24,501 | 79.9% | 0.1% |
| 0.44% | F Repro | 0.3 | 3.7 | 7.7 | 12.2 | 57.8 | 14.9 | 3.4 | $20,150 | $22,106 | 88.3% | 0.4% |
| 0.00% | Neonate | 12.6 | 12.5 | 12.5 | 25 | 12.5 | 12.5 | 12.4 | $19,319 | $28,654 | 62.4% | 0.0% |
| 0.09% | CD | 2.5 | 10.2 | 11.4 | 14.6 | 45.6 | 10.1 | 5.6 | $18,392 | $22,728 | 75.9% | 0.1% |
| 0.01% | Eye | 11.8 | 17.7 | 5.9 | 23.5 | 23.6 | 11.7 | 5.8 | $16,032 | $22,944 | 64.6% | 0.0% |
| 1.20% | Pregnancy | 0.7 | 5.2 | 20 | 27.4 | 43 | 3 | 0.7 | $13,249 | $15,899 | 74.1% | 0.9% |
| 94.10% | MISSING | 68.4 | 15.4 | 6.9 | 3.5 | 5 | 0.7 | 0.2 | $3,592 | $17,170 | 9.4% | 8.8% |

Fig. 15B

| | Without CD | With CD | Difference | Multiple |
|---|---|---|---|---|
| *Chronic Diseases* | | | | |
| Respiratory Disease (Asthma, COPD) | $29,622 | $37,985 | $8,363 | 1.28x |
| Cardiac Disease (CHF, CAD) | $32,990 | $40,899 | $7,909 | 1.24x |
| Diabetes | $27,271 | $33,710 | $6,440 | 1.24x |
| ESRD | $28,627 | $36,869 | $8,242 | 1.29x |
| High-Risk Pregnancy | $18,739 | $32,189 | $13,450 | 1.72x |
| Depression | $20,202 | $26,458 | $6,256 | 1.31x |
| *Trauma* | $41,927 | $52,578 | $10,652 | 1.25x |
| *Surprises* | | | | |
| Eye Disorders | $15,651 | $25,471 | $9,820 | 1.63x |
| Burns | $26,379 | $39,786 | $13,407 | 1.51x |
| ENT Disorders | $26,624 | $36,598 | $9,974 | 1.37x |
| Skin Disorders | $26,618 | $36,036 | $9,418 | 1.35x |
| HIV | $22,913 | $30,452 | $7,539 | 1.33x |

Fig. 16

APPLICATION OF BAYESIAN NETWORKS TO PATIENT SCREENING AND TREATMENT

RELATED APPLICATIONS

This application claims the benefit of U.S. Provisional Patent Application No. 61/247,937, entitled "Application of Bayesian Networks to Patient Screening and Treatment", filed Oct. 1, 2009, which is incorporated by reference herein in its entirety.

FIELD OF THE INVENTION

Embodiments of the invention relate generally to the field of Bayesian network modeling; and more particularly, to the use of machine-learned Bayesian networks to identify individuals at risk for a disorder and to identify those individuals most likely to benefit from intervention and treatment for the disorder.

BACKGROUND

A Bayesian belief network (BBN) is a directed graph and an associated set of probability tables. The graph consists of nodes and arcs. The nodes represent variables, input data for which can be discrete or continuous; however the BBN must segment continuous data into parameterized ranges. The arcs represent causal or influential relationships between variables. More specifically, a BBN is a probabilistic graphical model that represents a set of random variables and their conditional independencies. It is a way of describing complex, probabilistic reasoning.

Machine learning is a field of computer science that uses intelligent algorithms to allow a computer to mimic the process of human learning. The machine learning algorithm allows the computer to learn information structure dynamically from the data that resides in the data warehouse. The machine learning algorithms automatically detect and promote significant relationships between variables, without the need for human interaction. This allows for the processing of vast amounts of complex data quickly and easily.

The machine learning models can be scored in different ways: Minimum Description Length (MDL), also known as the Bayesian Information Criterion (BIC), as well as Bayesian Scoring (BDe). Minimum Description Length scoring provides a measure of the quality of a model. It trades off between goodness of fit and model complexity (parsimonious scoring). Goodness of fit is measured as the likelihood of the data given the model. Model complexity equals the amount of information required to store the model, subject to an inflator/deflator set by the user. The BBN networks and/or machine learning models have not been previously utilized in policy decision making processes of insurance plans or in selection of enrollees for disease management or care interventions.

SUMMARY OF THE DESCRIPTION

According to one aspect of the invention, health insurance claim data for a first group of individuals is obtained to generate a training corpus, including a training set of claim data and a holdout set of claim data. The first group of individuals represents enrollees of one or more health insurance plans and the health insurance claim data represents historic insurance claim information for each individual in the first group. A Bayesian belief network (BBN) model is created by training a BBN classifier using the training set of claim data using predetermined machine learning algorithms. K-fold cross-validation may also be used during the model training process to assess model robustness and feature selection. The BBN model is finally validated using the holdout set of claim data. A successfully validated BBN model can then be used to identify individual-specific risk of disorder and individual-specific likelihood of benefit from intervention and successful treatment for the disorder.

According to another aspect of the invention, a first set of claim data is received from a client, where the first set of claim data is associated with a first group of individuals representing enrollees of a first health insurance plan. A screening operation is performed using at least one screening Bayesian belief network (BBN) model based on the first set of claim data to identify a subset of individuals in the first group having risk characteristics associated with a disorder. Cost estimation is performed on the subset of individuals using at least one cost BBN model to produce enrollee specific cost estimates. These BBN models can consist of at least one screening BBN model and at least one cost BBN model that were trained using a predetermined machine learning algorithm based on a second, separate set of claim data associated with a second group of individuals of a second health insurance plan. The second set of claim data represents historic insurance claim information for each individual in the second group. The enrollee-specific estimates of risk and cost as developed using a BBN model trained on the second set are then transmitted to the client.

Other features of the present invention will be apparent from the accompanying drawings and from the detailed description which follows.

BRIEF DESCRIPTION OF THE DRAWINGS

Embodiments of the invention are illustrated by way of example and not limitation in the figures of the accompanying drawings in which like references indicate similar elements.

FIGS. 9A-9B are tables illustrating certain statistical results of screening models according to some embodiments of the invention.

FIGS. 11A-11B and 12-13 are tables illustrating certain statistical results of screening models according to some embodiments of the invention.

FIGS. 15A and 15B show expected cost outcomes given prior information as calculated by the cost models according to some embodiments of the invention.

FIG. 16 shows the expected annual cost differential, on an annual basis, for enrollees diagnosed with selected chronic conditions both with and without SUD, according to one embodiment.

DETAILED DESCRIPTION

Figure 1:
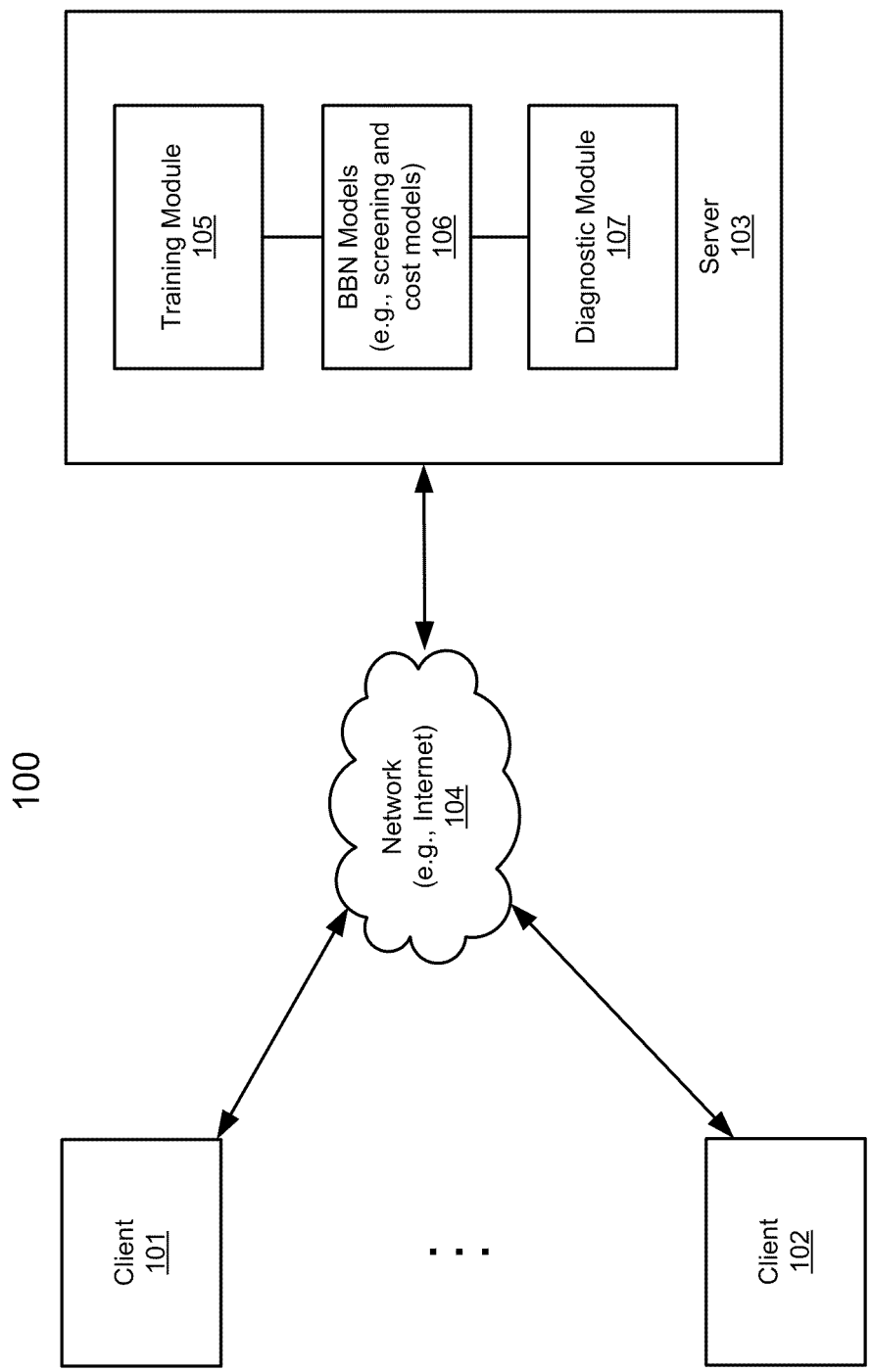
FIG. 1 is a block diagram illustrating a network system that can be used with an embodiment of the invention.

Various embodiments and aspects of the inventions will be described with reference to details discussed below, and the accompanying drawings will illustrate the various embodiments. The following description and drawings are illustrative of the invention and are not to be construed as limiting the invention. Numerous specific details are described to provide a thorough understanding of various embodiments of the present invention. However, in certain instances, well-known or conventional details are not described in order to provide a concise discussion of embodiments of the present inventions.

Reference in the specification to "one embodiment" or "an embodiment" means that a particular feature, structure, or characteristic described in conjunction with the embodiment can be included in at least one embodiment of the invention. The appearances of the phrase "in one embodiment" in various places in the specification do not necessarily all refer to the same embodiment.

According to some embodiments, a mechanism is provided for creating a model to identify individuals at risk for a disorder, to estimate future utilization patterns and costs for an individual with the disorder, and/or to identify individuals with the disorder who are most likely to benefit from intervention and successful treatment for the disorder. As used herein, the term "disorder" refers to any physical or mental disease, disorder, or syndrome. According to one embodiment, data (e.g., claim data) about a group of individuals is obtained, where the data includes data relevant to the disorder, demographic information, and general health data. The group of individuals may be associated with one or more insurance plans provided from one or more insurance providers (e.g., same or different insurance providers). Such data may be provided by one or more health insurance providers or some other claim data providers. One or more machine learning algorithms are utilized to build a Bayesian Belief Network (BBN) that identifies individuals at risk for the disorder, which can estimate prospective utilization and cost for individual enrollees, and/or identifies individuals with the disorder who are most likely to benefit from intervention and treatment for the disorder. The group may include enrollees in one or more health insurance plans, and the data may include historic insurance claim information for each enrollee. For example, the claim information may be clinical, demographic, and utilization information, such as hospitalizations, outpatient services, procedure codes, diagnostic codes, diagnostic-related group codes, drugs prescribed, chronic conditions, co-morbid conditions, interval between encounters, historic cost and utilization trends, enrollee industry, employment status, sex, age, region of the country, urban or rural setting, and relation to the insured.

Such a model may be created from historic insurance claim information for enrollees in a health insurance plan by obtaining insurance claim information for insurance plan enrollees that includes individuals both with and without the disorder, defining the type of data associated with a diagnosis of the disorder, identifying enrollees with the disorder, separating the data for the subgroup into a training set and a holdout set, employing one or more machine learning algorithms on the training set data to train a series of BBNs, evaluating each BBN to identify the best BBN network and structure and to select the most robust network, and validating the selected BBN on the holdout set data. The selected BBN model is then utilized for cost and/or treatment estimates for the identified type of individuals.

Embodiments of the present application are to explore the use of machine learning and Bayesian classification models to develop broadly applicable screening and stratification models to guide the identification and management of health plan enrollees with Substance Use Disorder (SUD), also known as Chemical Dependency (CD). While the high costs and morbidities associated with SUD are understood by payors, who manage it through utilization review, acute interventions, coverage and cost limitations, and disease management, the literature shows mixed results for these modalities in improving patient outcomes and controlling cost.

FIG. 1 is a block diagram illustrating a network system that can be used with an embodiment of the invention. Referring to FIG. 1, network system 100 includes, but is not limited to, one or more clients 101-102 communicatively coupled to server 103 over network 104. Network 104 may be a local area network (LAN) or a wide area network (WAN) such as the Internet. Clients 101-102 may be implemented as any kind of devices, such as desktops, laptops, mobile communications devices, etc. Server 103 may be a Web server or an application server.

In one embodiment, server 103 includes, but is not limited to, a training module 105, one or more BBN models 106, and a diagnostic module 107. Training module 105 is configured to obtain a set of insurance claim data as a training corpus, for example, from one or more insurance providers, Centers for Medicare or Medicaid Services (CMS), or other data providers such as Thomson-Reuters' MarketScan®, to train and produce one or more BBN models 106 using a machine learning algorithm, such as, for example, the FasterAnalytics™ software suite from DecisionQ Corporation of Washington, D.C. The machine learning algorithms use a heuristic search mechanism and information scoring metric to automatically detect and promote significant relationships between variables, without the need for human interaction. This allows for the processing of vast amounts of complex data quickly and easily. The BBN models 106 are then utilized by diagnostic module 107 to provide an estimate of cost with or without medical treatment. Such a cost estimate may be utilized in insurance policy decision making processes (e.g., health insurance enrollment decisions).

Figure 2:
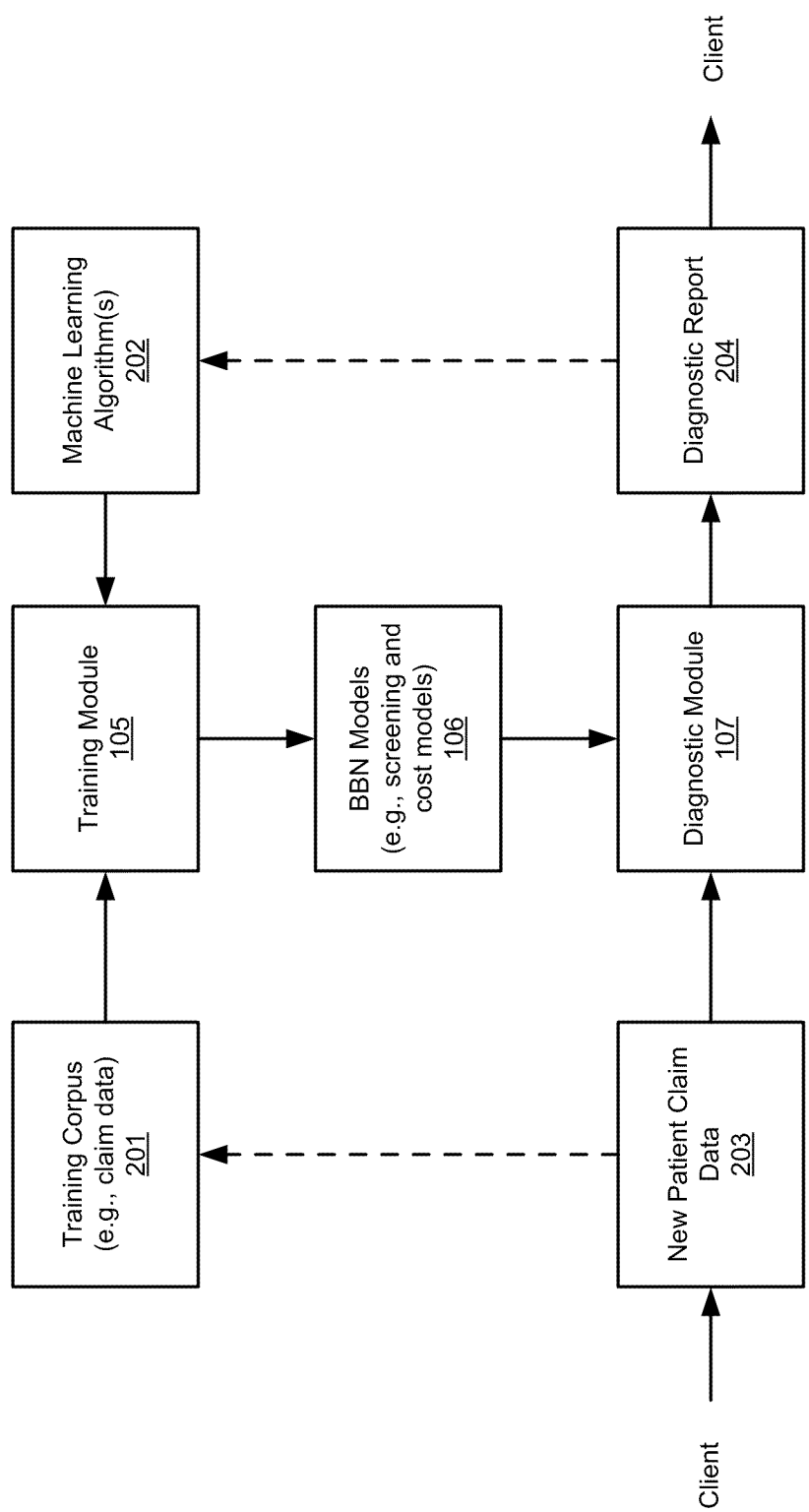
FIG. 2 is a block diagram illustrating a system for modeling BBN models for diagnosis according to one embodiment of the invention.

FIG. 2 is a block diagram illustrating a system for modeling BBN models for diagnosis according to one embodiment of the invention. For example, system 200 may be implemented as part of server 103 of FIG. 1. Referring to FIG. 2, system 200 includes training module 105 configured to train a set of training corpus 201, which may represent a set of health insurance claim data obtained from one or more insurance providers or other entities, to generate one or more BBN models 106 using one or more machine learning algorithms 202. In one embodiment, BBN models 106 include at least one screening model to identify a subset of enrollees having certain risk characteristics and at least one cost model to provide a cost estimate for the identified enrollees. BBN models 106 may be utilized subsequently by diagnostic model 107 to perform diagnosis on new set of claim data 203 and to provide a diagnostic report 204 to the client. Data 203 and diagnostic report 204 may be fed back to the training system for future training and/or adjustment of BBN models 106.

Figure 3:
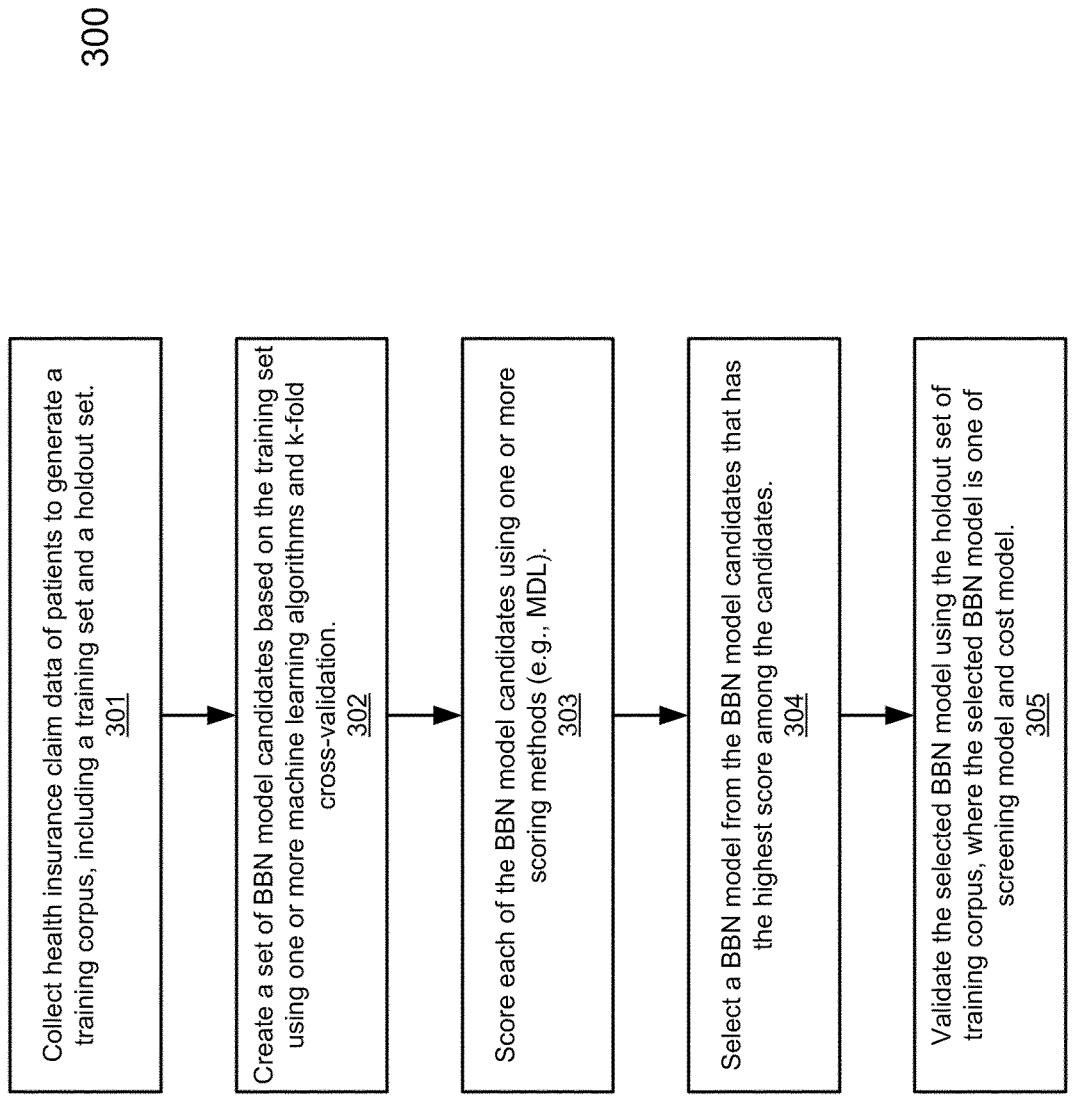
FIG. 3 is a flow diagram illustrating a method for creating a BBN model according to one embodiment of the invention.

FIG. 3 is a flow diagram illustrating a method for creating a BBN model according to one embodiment of the invention. For example, method 300 may be performed by training module 105 of FIG. 2. Referring to FIG. 3, at block 301, a set of health insurance claim data of patients is collected, for example, from one or more health insurance related providers or claim data providers, to generate a training corpus, including a training set and a holdback set. At block 302, a set of BBN model candidates are created based on the training set using one or more machine learning algorithms. At block 302, k-fold cross-validation may be used, along with qualitative and classical statistic methods, as a feature selection method in order to optimize the network. At block 303, each of the BBN models is scored using one or more scoring methods, such as Minimum Description Length (MDL), also known as the Bayesian Information Criterion (BIC), as well as Bayesian Scoring (BDe). At block 304, a BBN model having the highest score among all is selected as the final candidate from the BBN candidates. At block 305, the selected BBN model is validated using the holdout set of training corpus. Note that method 300 may be utilized to train a screening model and/or a cost model described throughout this application.

In one embodiment, BBN models (e.g., BBN models 106), also referred to as predictive models, are built by applying a set of heuristics to generate predictive models with different conditional independence assumptions. The conditional independence assumptions are represented as a directed acyclic graph, wherein the structure of the network represents a hierarchy of conditional independence which allows the user to identify the best estimators of a given outcome. The predictive models encode the joint probability distributions of all of the variables in the clinical/claim data set from the previous clinical trials/claim processes by building a network of conditional probabilities. The predictive models provide a network incorporating parent-child relationships between nodes. The network is queried to provide estimates for posterior probabilities given a priori knowledge, and tested for accuracy using data withheld from the training model. The predictive models are constructed using a machine learning algorithm that supports a Minimum Description Length (MDL) scoring metric for network optimization. MDL scoring ensures that the final model represents the most likely model given the data used for learning and the model variations under consideration.

MDL scoring is based in probability and information theory and statistics and is equivalent to the Bayesian Information Criterion. MDL compares the goodness of fit of the model, as calculated using Shannon's Mutual Information, to the complexity of the model, represented by the bit length required to store the model in memory. This is commonly referred to in modeling as a parsimonious approach: all things being equal a simpler model is a better model. The objective is to select the most likely model given the available data, thus optimizing robustness.

Machine learning algorithms allow computer to learn dynamically from source data that can reside in a file, a database, or a data warehouse. The machine learning algorithm automatically detects, evaluates, and promotes significant relationships between variables without the need for human interaction using a scoring algorithm intended to optimize the network for robustness, thus learning information structure natively from data without prior specification by the operator. This allows for the processing of vast amounts of complex data quickly and easily into a tractable BBN. The structure of the network provides the user with immediate knowledge about the nature of the problem set and the relative significance of variables to the outcome of interest.

An embodiment of the invention utilizes a step-wise modeling process to optimize the accuracy of the BBN models. The development of the BBN models is an iterative process consisting of several steps, the end product of which is a predictive model that supports subsequent dynamic re-training with new data (e.g., new data 203). The process streamlines variable selection and preparation to produce the optimum outcome.

In at least one embodiment of the invention, model creation begins with preliminary modeling to identify appropriate machine learning parameters and data quality issues. A base level of association in the dataset and obvious associations that are interfering with the base level (confounding features) are also identified. Feature analogs (i.e., features that are proxies for one another and reduce accuracy or utility) are identified and removed by the operator. Next, an operator uses the pruned features to train a new classifier in order to assess and set appropriate machine learning parameters. Appropriate changes may be made to the data set, including the removal of analogs and confounding features and further binning. The model is explored relative to the literature and domain expertise as a "check" and to analyze relationships. Linear naïve modeling may also be performed on dependent outcomes of interest to identify the relative contribution of features. A quantitative contribution report is also prepared in at least one embodiment. In one embodiment, training data is randomized and segmented in order to score feature selection using k-fold cross-validation. In k-fold cross-validation, the data set is repeatedly split into matching training and testing sets at random. The training set is used to train a BBN classifier and the testing set is used to score model robustness for features of interest.

Following the pruning and qualitative validation process, final focused modeling is performed. During focused modeling, heuristic search is performed using only subsets of variables identified in prior steps discussed in the previous paragraph. As a result, a network is obtained that is more focused than the network produced in the prior steps. By excluding certain variables, the remaining variables are explored more exhaustively. The focused model is explored and preliminary reports are automatically created. In at least one embodiment, manual modeling may also be performed to enhance the focused model. Specifically, the structure of relationships is changed manually using a user interface to incorporate expert information beyond what the data contains.

Figure 4:
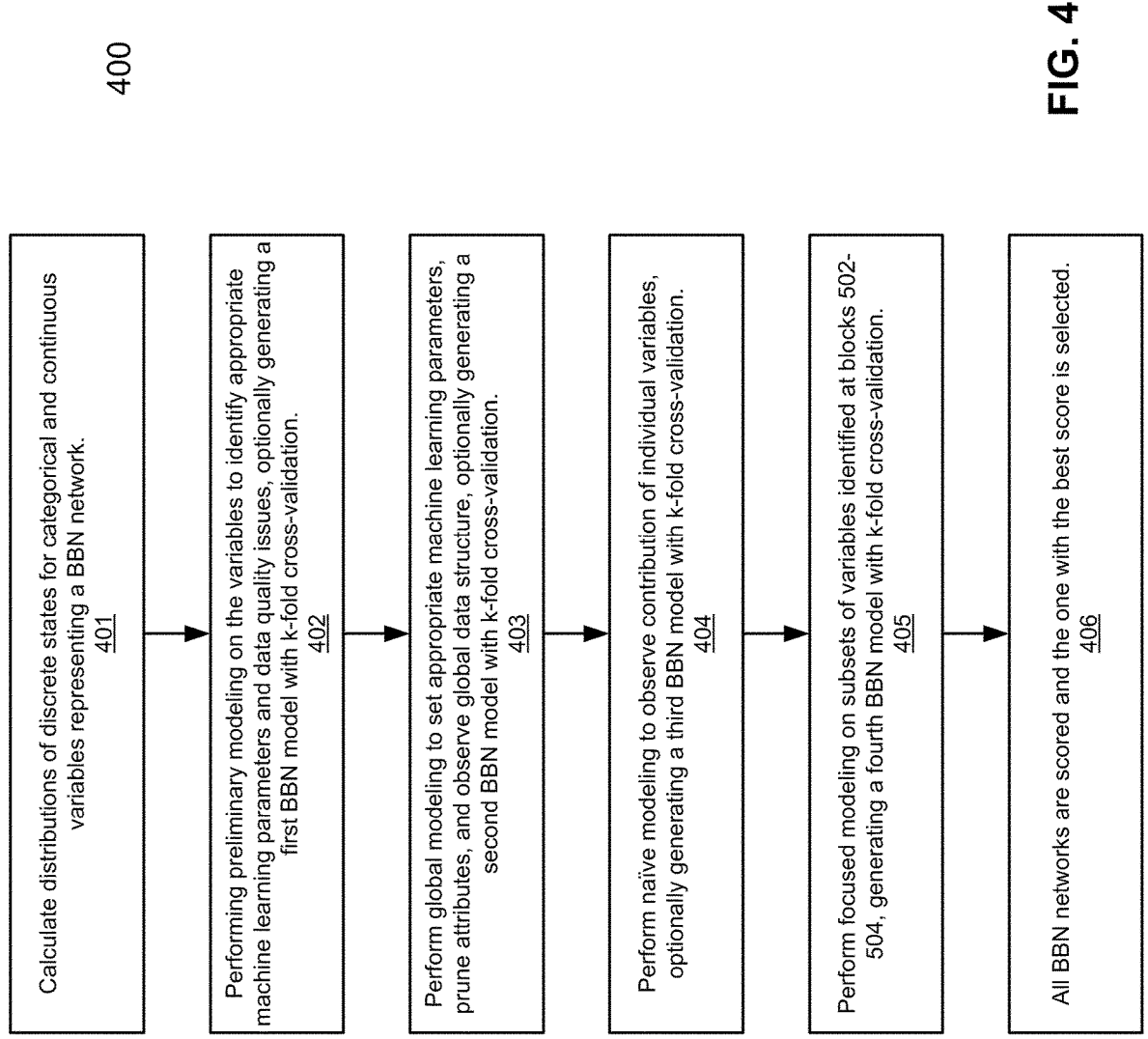
FIG. 4 is a flow diagram illustrating a method for creating a BBN model according to an alternative embodiment of the invention.

FIG. 4 is a flow diagram illustrating a method for creating a BBN model according to an alternative embodiment of the invention. For example, method 400 may be performed as part of operations involved in blocks 302-304 of FIG. 3. Referring to FIG. 4, at block 401, distributions of discrete states are calculated for categorical and continuous variables to be incorporated in the machine-learned BBN network. At block 402, preliminary modeling is performed on the variables to identify appropriate machine learning parameters and data quality issues, optionally generating a first BBN model. At block 403, global modeling is performed to set appropriate machine learning parameters, prune attributes, and observe global data structures, optionally generating a second BBN model. At block 404, naïve modeling is performed to observe contribution of individual variables, optionally generating a third BBN model. At block 405, focused modeling is performed on subsets of variables identified above, generating a fourth BBN model. Throughout the process, k-fold cross-validation is used to assist in feature selection. At block 406, all BBN models are scored and the one with the highest score is selected as the final candidate.

Once the best possible BBN model is selected, according to one embodiment, additional k-fold cross-validation is performed, where a classifier is trained on each of the training sets created in the data preparation step using the same data discretization and modeling parameters. Each corresponding test set is used to create a set of case-specific predictions. Moreover, a receiver operating characteristic (ROC) curve is plotted for each test exercise to calculate classification accuracy. In at least one embodiment, a 10% holdback dataset is withheld from the initial dataset (e.g., training corpus 201) to be used for prospective validation upon completion of k-fold cross-validation. Upon completion of cross-validation, the best model is documented in an XML format for deployment. The relevant learning parameters and modeling log files are stored if audits are performed in the future. All cross-validation files are also stored for future audits; and, a report summarizing the results is prepared.

In at least one embodiment, the network is validated using a cross-validation (e.g., train-and-test ten-fold) methodology. The cross-validation is performed, where multiple (e.g., ten) unique sets of data are used that have been randomized in 90% train/10% test pairs. This produces classification accuracy estimates across ten exercises and calculates the classification error. Predictive values are calculated by classifying the outcome for a given instance and comparing this prediction to the known value in an independent test set. The test set predictions are used to calculate a ROC curve and confusion matrix by threshold for each test set by the clinical feature of interest. The ROC curve is calculated by comparing the predicted value for each feature of interest to the known value in the test set on a case-specific basis. The ROC curve is used to calculate the area-under-the-curve (AUC), a metric of overall model quality, and positive predictive value (PPV), a measure of the probability that a positive is a true positive given a specified probability threshold for the variable of interest.

In signal detection theory, a receiver operating characteristic (ROC), or simply ROC curve, is a graphical plot of the sensitivity, or true positive rate, vs. false positive rate (1—specificity or 1—true negative rate), for a binary classifier system as its discrimination threshold is varied. The ROC can also be represented equivalently by plotting the fraction of true positives out of the positives (TPR=true positive rate) vs. the fraction of false positives out of the negatives (FPR=false positive rate). Also known as a Relative Operating Characteristic curve, because it is a comparison of two operating characteristics (TPR & FPR) as the criterion changes.

ROC analysis provides tools to select possibly optimal models and to discard suboptimal ones independently from (and prior to specifying) the cost context or the class distribution. ROC analysis is related in a direct and natural way to cost/benefit analysis of diagnostic decision making. ROC analysis has been used in medicine, radiology, and other areas for many decades, and it has been introduced relatively recently in other areas like machine learning and data mining.

A classification model (classifier or diagnosis) is a mapping of instances into a certain class/group. The classifier or diagnosis result can be in a real value (continuous output) in which the classifier boundary between classes must be determined by a threshold value, for instance to determine whether a person has hypertension based on blood pressure measure, or it can be in a discrete class label indicating one of the classes.

An ROC curve can be used to represent quality of an outcome of a test for a given set of data. For example, the accuracy of the test depends on how well the test separates the group being tested into those with and without the disease in question. Accuracy is measured by the area under the ROC curve. The area measures discrimination, that is, the ability of the test to correctly classify those with and without the disease. Consider the situation in which patients are already correctly classified into two groups. A user may randomly pick one from the disease group and one from the no-disease group and do the test on both. The patient with the more abnormal test result should be the one from the disease group. The area under the curve is the percentage of randomly drawn pairs for which this is true (that is, the test correctly classifies the two patients in the random pair).

Figure 5:
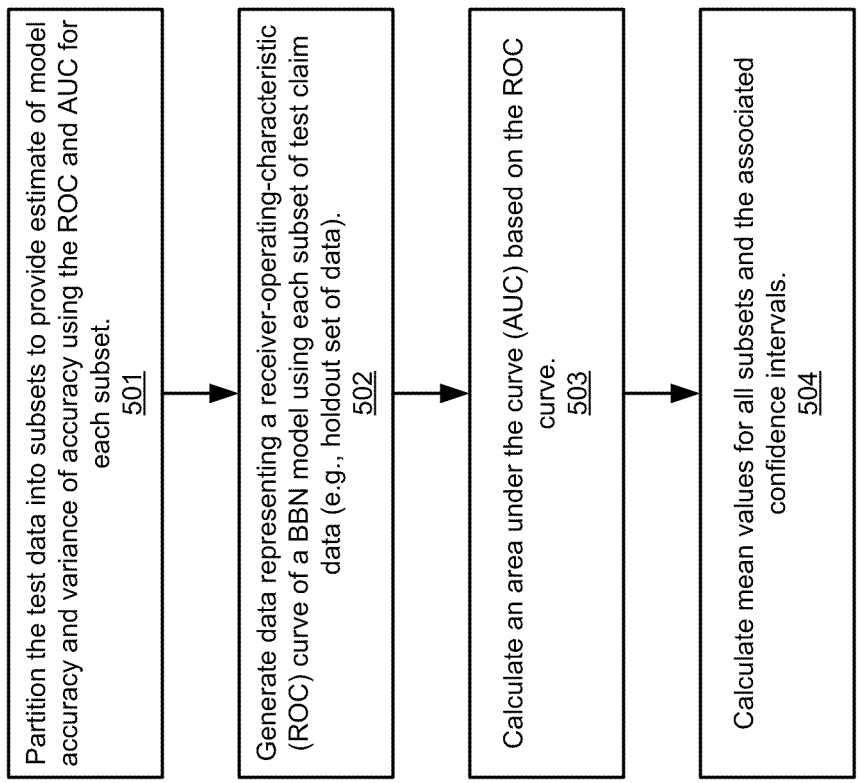
FIG. 5 is a flow diagram illustrating a method for validating a BBN model according to one embodiment of the invention.

FIG. 5 is a flow diagram illustrating a method for validating a BBN model according to one embodiment of the invention. For example, method 500 may be performed as part of operations involved at block 305 of FIG. 3 or as part of the training process in method 400. Referring to FIG. 5, at block 501, data representing an ROC curve of a BBN model is generated using a set of test claim data (e.g., holdout set of data), which may be obtained from one or more health insurance plans provided by one or more insurance providers or other claim data providers. At block 502, an AUC is calculated based on the ROC curve. At block 503, the test data is partitioned into subsets to provide estimate of model accuracy and variance of accuracy is calculated using the ROC and AUC for each subset. At block 504, mean values for all subsets and the associated confidence intervals are calculated, where the mean values are utilized to determine the quality of the BBN model.

Figure 6:
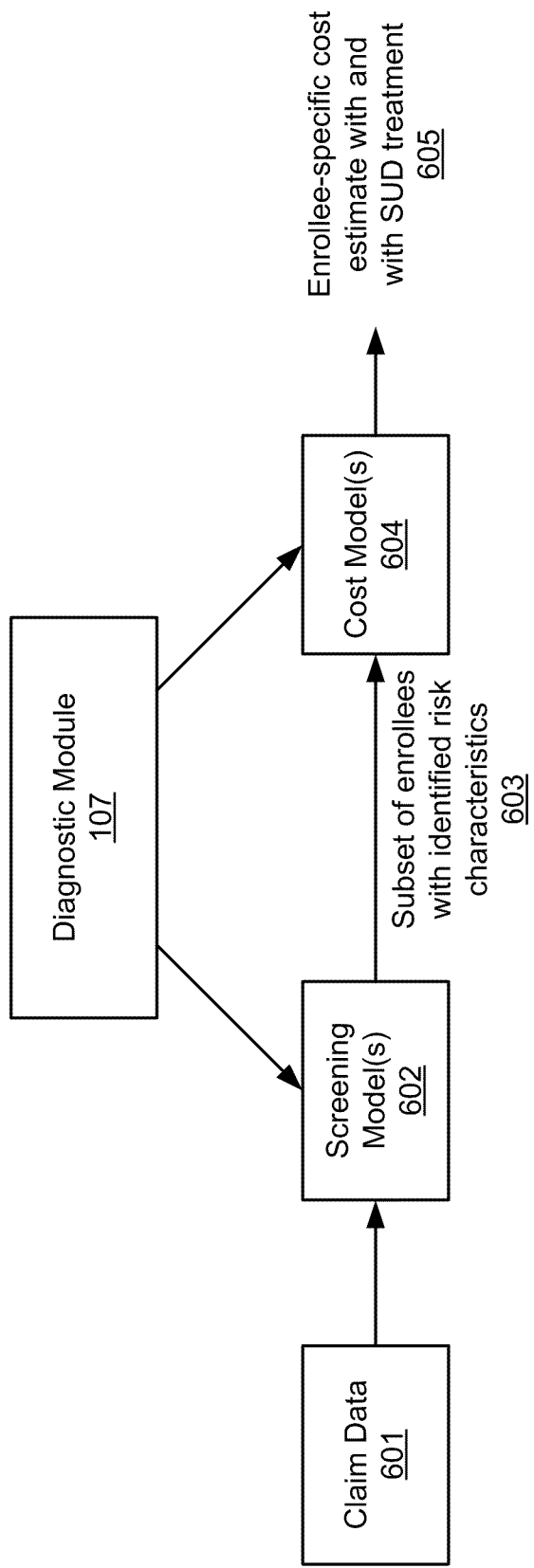
FIG. 6 is a block diagram illustrating a diagnostic system according to one embodiment of the invention.

Once the BBN models (e.g., screening models and cost models) have been created, such models can be used in subsequent diagnosis. FIG. 6 is a block diagram illustrating a diagnostic system according to one embodiment of the invention. For example, system 600 may be implemented as part of diagnostic system of FIG. 1. Referring to FIG. 6, a new set of claim data 601 of a health insurance plan is input into screening model 602 by diagnostic module 107, which identifies a subset 603 of enrollees with identified risk characteristics. The subset 603 is then input into cost model 603, which generates enrollee-specific cost estimate 605 with and without intervention and/or medical treatment.

Figure 7:
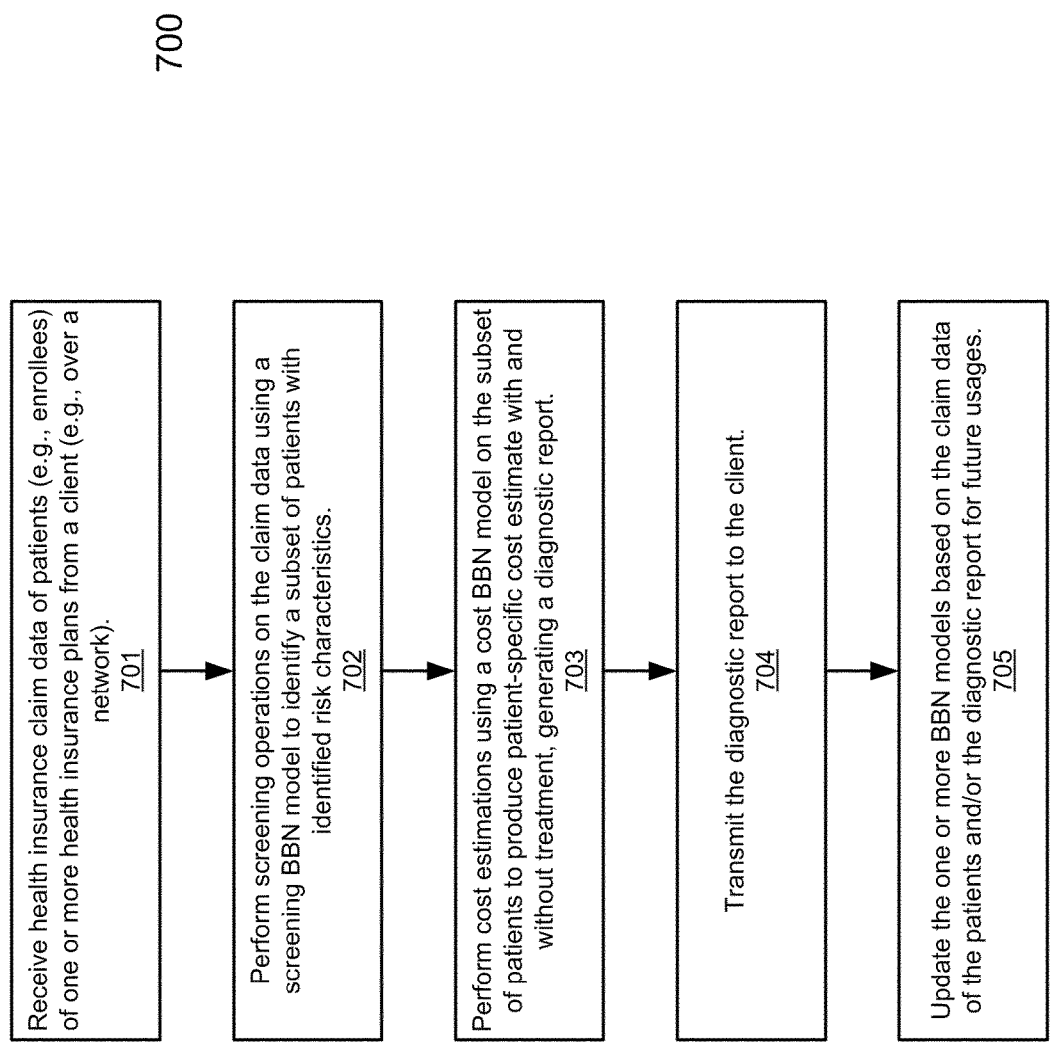
FIG. 7 is a flow diagram illustrating a method for diagnosis according to one embodiment of the invention.

FIG. 7 is a flow diagram illustrating a method for diagnosis according to one embodiment of the invention. For example, method 700 may be performed by system 600 of FIG. 6. Referring to FIG. 7, at block 701, health insurance claim data of patients of one or more health plans (e.g., enrollees) is received from a client. In response, at block 702, screening operations are performed using a screening BBN model to identify a subset of patients with identified risk characteristics, which may be related to a particular disorder. At block 703, cost estimation is performed using a cost BBN model on the subset of patients to produce patient-specific cost estimate with and/or without intervention and/or medical treatment, generating a diagnostic report, which is transmitted to the client at block 704. At block 705, the claim data and/or the diagnostic report outcomes are fed back to the modeling system for future modeling and/or machine learning algorithm adjustment as needed.

According to some embodiments of the invention, the techniques described above can be applied to a variety of situations. For example, the techniques described above can be applied to multivariate probabilistic (Bayesian) networks to SUD screening, cost estimation, and stratification. The techniques can be used to explore the use of machine learning and Bayesian classification models to develop broadly applicable screening and stratification models to guide the identification and management of health plan enrollees with SUD. While the high costs and morbidities associated with SUD are understood by payors, who manage it through utilization review, acute interventions, coverage and cost limitations, and disease management, the literature shows mixed results for these modalities in improving patient outcomes and controlling cost. The above techniques can be used to evaluate the use of data mining methods' potential to address some of the shortcomings of conventional practice.

For the purpose of evaluation, according to one embodiment, machine learning algorithms such as the one available from DecisionQ corporation (Washington, D.C.) are used to build Bayesian network models of representative sample of data provided from Thomson-Reuters' MarketScan® consisting of 185,322 enrollees with three full years of insurance claims records. Data sets were prepared and a step-wise learning process was used to train a series of Bayesian Belief Networks (BBNs). The BBNs were validated using a portion such as a 10% holdout set. As a result, the networks were highly predictive, with the screening BBNs producing AUC for SUD positive of 0.948 (95% Confidence Interval (CI): 0.944-0.951) and 0.736 (95% CI: 0.721-0.752), respectively, and SUD negative of 0.951 (95% CI: 0.947-0.954) and 0.738 (95% CI: 0.727-0.750), respectively. The cost estimation models produced AUCs ranging from 0.72 (95% CI: 0.708-0.731) to 0.961 (95% CI: 0.95-0.971). The inventors have successfully modeled a large, heterogeneous population of commercial enrollees, applying state-of-the-art machine learning technology to develop complex and accurate multivariate models that support near-real time scoring of novel payor populations based on historic claims and diagnostic models. The initial validation results indicate that we can stratify enrollees with SUD diagnoses with a high degree of sensitivity and specificity.

In 2007, an estimated 19.9 million persons aged 12 or older were current illicit drug users and 17.0 million individuals were heavy drinkers. Results from one recent study indicate that the risk for cocaine dependence is 5%-6% among all those who have used the drug. While it is generally acknowledged that SUD has high health care costs, co-morbidities, and economic costs to the nation, the development of systematic approaches to management and intervention in this population has been handicapped by what is still a limited knowledge of disease mechanics compared to disease such as cancer and heart disease, where individuals tend to have a more advanced understanding of disease physiology and genetics supporting evidence-based population intervention and treatment models. While individuals are making tremendous strides in understanding the genetics and physiology of SUD, there is still a need to enhance the toolset for intervention and management. Further, it has been documented that SUD contributes not only to behavioral health costs but also to overall medical costs.

One of the purposes of these experiments is to explore the use of machine learning and Bayesian classification models to develop broadly applicable screening and stratification models to guide the identification and management of health plan enrollees with SUD. While the high costs and morbidities associated with SUD are understood by payors, who manage it through utilization review, acute interventions, coverage and cost limitations, and disease management, the literature shows mixed results for these modalities in improving patient outcomes and controlling cost. There has been a selection bias documented in disease management that may contribute to reduced success rates, as the literature shows that in appropriately targeted populations, disease management and interventions can prove very successful. However, the literature is also severely critical of the current state of the art in developing personalized, stratified models of care in behavioral health, as evidenced by the disappointing results in the MATCH study, and there is vigorous debate in the literature over the benefit of these types of models. One objective was to evaluate the use of data mining methods' potential to address some of the shortcomings of current practice.

An embodiment of the invention has the ability to address many of these limitations by supporting more complex rule sets that can effectively account for the inherent complexity of co-morbid interactions. Further, it has been focused on developing tools from a claims database since this represents a common substrate available to both payors and providers, as the literature often laments the lack of access to good data sets for evaluation. By focusing on the most widely available data, one can develop a set of methods and tools that have the potential to improve patient screening, risk stratification, and therapy selection to address current shortcomings in practice by developing an individualized model of risk stratification using broad populations and readily available data.

While there is extensive literature on the co-morbidities and impact that SUD has on other acute and chronic conditions, these are multiple, complex relationships that are often studied in a bi-variate context. Assembling these into a robust, a useful rule set is non-trivial. Some work has been done using regression modeling and clustering, however these methods suffer from limitations with respect to their ability to codify complex nonlinear relationships, ingest and model large sample sizes, and provide transparent outputs to users.

According to one embodiment, machine learned Bayesian Belief Network (BBN) probabilistic classifiers are utilized because they address several of these key issues. BBNs allow for the representation of complex, nonlinear systems in a transparent format that is tractable, or easily comprehensible, to the user. It has been shown that BBNs are effective at representing complex biological systems in a robust manner. However, the use of Bayesian networks has historically been limited by a high level of inherent computational complexity. However, the advent of increased computational power and machine learning algorithms allow individuals to overcome these challenges and develop novel BBNs directly from large, heterogeneous training cohorts.

For the purpose of evaluation, machine learning algorithms (e.g., FasterAnalytics™ software from DecisionQ) are used to build Bayesian network models of representative sample of data provided from Thomson-Reuters' MarketScan®. The sample contained detailed insurance claim information on 400,000 randomly selected MarketScan enrollees over the years 2004, 2005, and 2006. The data records (which are de-identified) have information on demographics, inpatient admissions (including detailed procedure codes, diagnosis codes and charges), outpatient services, and pharmacy claims. The sample is restricted to the 185,322 individuals who remained enrolled all three years. The resulting models are used to identify key relationships and identify combinations of factors to calculate both the individual risk probability of SUD as well as an individual estimate of total annual future claims given demographic factors and co-morbid conditions. Future claims estimates can also be derived by making assumptions about treatment and the impact that treatment may have on utilization.

In this example, Thomson Reuters provided a set of forty-two tables of information on a randomly selected sample of 400,000 enrollees, aged 18 to 65, from their MarketScan database. The data, which cover the years 2004, 2005, and 2006, include details on each inpatient, outpatient, and pharmacy claim together with demographic information by enrollee. The database is de-identified but each record has a unique identification field suitable for matching information by enrollee across the various tables.

The process began with 29.7 million data records describing three years of clinical history of 400,000 enrollees. Therefore the process of arranging selected elements by enrollee and organizing into a single record per enrollee for analysis ("flattening" the data) for modeling was non-trivial. To accomplish it SAS routines were used to merge tables within category, but across years. Each table was sorted by encounter date and used a series of Java applications (operating across a JDBC-ODBC bridge) to extract and aggregate required database fields by unique enrollee. The Java routines output their results to comma-delimited text files, which can be incorporated into a Microsoft Access database.

Upon analysis, it was observed that 185,322 of the 400,000 MarketScan populations were present in all three years of data. The sub-group was used as study population. This provided us with a well-defined, representative cohort of adult enrollees. A randomly selected training set of 166,999 (roughly 90%) was used for model building. The remaining 10% or 18,623 individuals became the holdout set, which were used subsequently to validate the models. A set of ICD-9-CM codes was identified directly associated with diagnosis of SUD. A database enrollee is defined as having SUD if any of the diagnosis codes in the set appear in a claim record, either as primary diagnosis or non-primary diagnosis. All enrollees in the three year cohort that met these criteria were coded as such in the final database.

The prepared data set is used to train a series of BBNs to estimate individual risk of SUD as well as expected future utilization. BBNs have increased in popularity as a method to classify and interpret complex clinical and pathologic information because they more accurately reflect the non-linear and multi-factorial nature of biology. A Bayesian network encodes the joint probability distribution of all the variables in a domain by building a network of conditional probabilities. It uses conditional independence assumptions to make the representation tractable. The networks are directed graphs which incorporate parent-child relationships between nodes. Essentially, they provide a hierarchy of how the knowledge of a priori evidence influences the downstream likelihood of an event (e.g., "I know that enrollee X has hypertension, therefore the probability of kidney disease relative to my overall population is y"). The model is tractable to the user because it is a transparent, graphical representation of these probabilities that a user can interpret, unlike a neural network which uses complex calculations which cannot be represented to the user and is thus opaque.

In one embodiment, machine learning is used to calculate prior probabilities and identify the structure of the BBN. Prior probabilities are derived from the data to be modeled by calculating distributions of discrete states for categorical variables or using binning to convert continuous variables into categorical variables. A heuristic search method is used to generate hypothetical models with different conditional independence assumptions in order to identify the best model structure. The heuristic search method used in this study benefits from at least two proprietary advances, one that uses a more efficient caching and query system that allows individuals to consider an order of magnitude more data, the second being a very efficient search architecture that provides additional flexibility in searching for the optimal model structure. These improvements have been shown to perform 1%-5% better than a standard heuristic algorithm in terms of model quality score.

The heuristic search algorithms are utilized in a step-wise modeling process to optimize the robustness and utility of each BBN. The objective of this process is to produce the most robust classifier with respect to identification of SUD or stratification into expected utilization categories through better attribute selection and continuous testing.

As described above, this process can be summarized as the following operations: 1) preliminary modeling identifies appropriate machine learning parameters, data quality issues, and confounding attributes that reduce model accuracy; 2) global modeling sets appropriate machine learning parameters, prunes attributes, and allows investigators to observe global data structure; 3) naïve modeling operates with an assumption that features driving a specific dependent outcome of interest are mutually independent, therefore providing insight into the direct contribution of individual features; and 4) focused modeling runs on subsets of variables identified in the prior steps to derive a more focused BBN than that obtained in global modeling. Continuous testing is used to score networks with the objective of identifying the best network and structure, with the objective of balancing between reducing the risk of over-fitting while exploring features exhaustively.

Given the high dimensionality of the data being used and the problem under consideration, it was recognized that in order to maximize predictive power, a series of different classifiers should be trained and independently evaluated using the test set, and then the best classifiers for disease screening and cost estimation should be selected and used to derive insights and rules for screening and management. As a result, two sets of models were produced: 1) screening models for the estimation of risk of SUD in enrollees in a broad population; and 2) cost/treatment models for the estimation of utilization, cost, and therapy response within different enrollee subsets.

The network may be validated using a holdout data set of enrollees for inter-set validation. In one embodiment, the validation set is further broken into multiple (e.g., ten) different sub-sets to provide an estimate of both classifier accuracy and variance of classifier accuracy. The test set predictions were then used to calculate Receiver-Operating-Characteristic (ROC) curves (sensitivity vs. specificity) for each model. The ROC curve was calculated by comparing the predicted value for each variable to the known value in the test set on a case-specific basis and then used to calculate area-under the curve (AUC), a metric of overall model quality.

Some basic statistics are calculated to describe the study population. Of total enrollees in 2004, 23.9% dropped out in 2005, and 53.7% had dropped out by 2006. Of enrollees who had any SUD diagnosis in 2004, 21.3% dropped out in 2005, and 52.5% had dropped out by 2006. These numbers are essentially comparable, indicating that enrollees with a diagnosis of SUD leave coverage at about the same rate as the general population. Looking at those members of the population who remained enrolled for the entire study period, 4.04% had an SUD diagnosis (either primary or non-primary, inpatient or outpatient) during the study period, and in each of 2004, 2005, and 2006 the rate of SUD diagnosis ranged from 1.5%-1.7%.

Having identified the SUD enrollees, according to one embodiment, machine learning is invoked to build a Bayesian classifier to describe the associations in the commercial enrollee population. Many clinical and demographic factors are involved in making a diagnosis of SUD. Estimating related utilization involves multiple diseases and multiple diagnoses with multiple mechanisms. BBNs allow one to represent these complex relationships in an efficient and user-friendly manner. Each classifier trained has a unique hierarchy of information, or structure. These structures help to identify how different variables influence the expected likelihood of outcome, such as SUD or expected cost range. The structure of the BBN is meaningful in itself, in that it provides a hierarchy of conditional dependence, or the likelihood of a given outcome given known information. It is important to note that this is not causality, but rather conditional dependence, which can be thought of as co-occurrence.

Figure 8A:
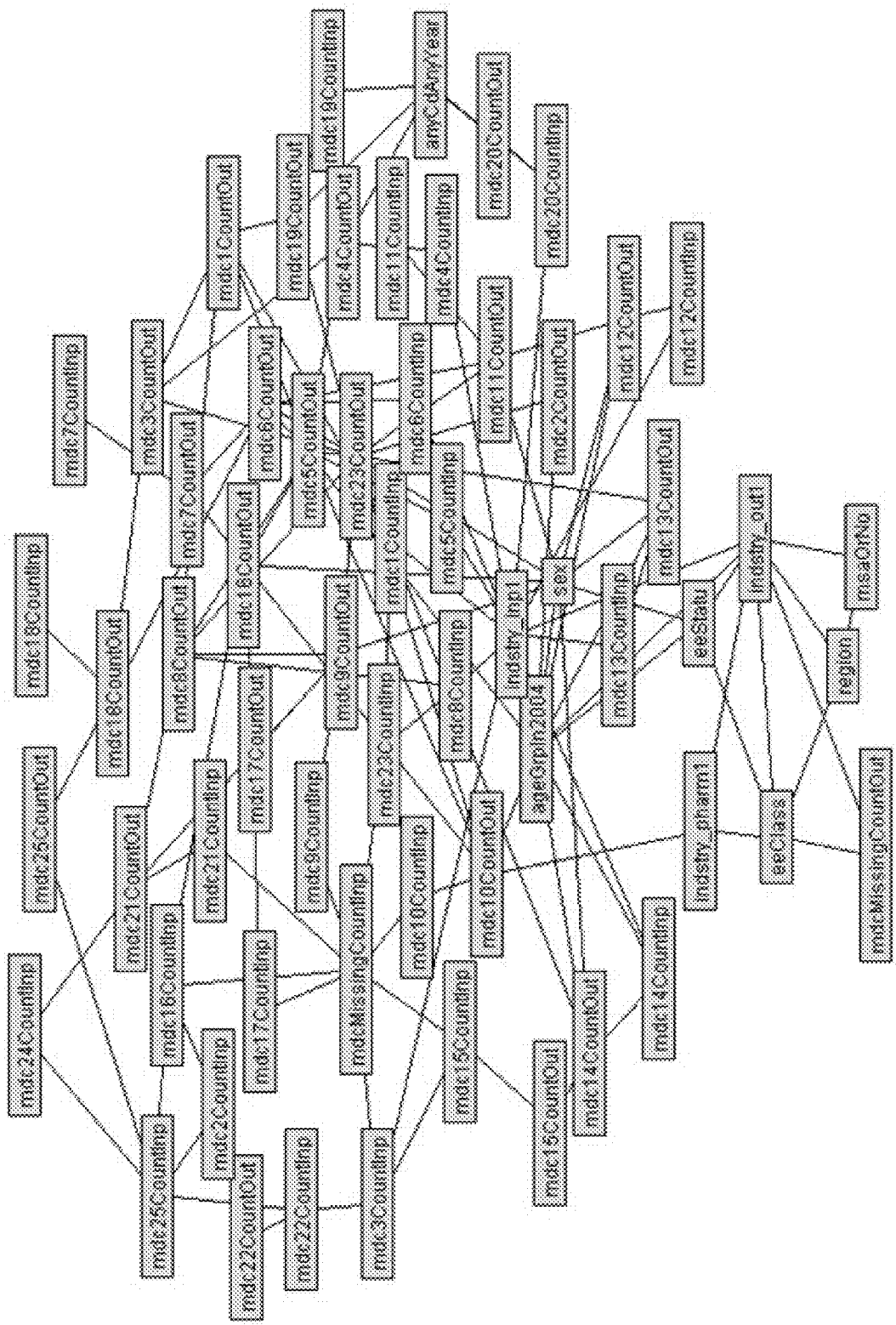
FIGS. 8A and 8C are diagrams illustrating structures of screening models according to some embodiments of the invention.

FIG. 8A is a diagram illustrating one potential structure of a BBN screening model according to one embodiment. In this model, referring to FIG. 8A, each enrollee data record has been flattened to examine the presence or frequency of individual values of Major Diagnostic Category (MDC), a classification developed by CMS and used in the Thompson Medstat database to group diagnosis into major categories (e.g., SUD or Cardiovascular Disease). In FIG. 8A, a user can interpret structures relative to outcomes of interest; e.g., mdc20CountOut, mdc20CountInp, and anyCDAnyYear. These variables represent the count of outpatient SUD diagnoses in a given claims year, the count of inpatient SUD diagnoses in a given claims year, and whether or not the enrollee had any diagnoses of SUD during the study period.

These outcomes have conditional dependence (represented by lines, or arcs) with the following first order associates: industry_inp1 (enrollee industry), mdc19CountInp and mdc19CountOut (count of inpatient and outpatient behavioral health disorder diagnoses), and mdc4CountOut (count of outpatient diseases of the respiratory system). These first-order predictors are not necessarily causative of SUD, but rather are the most information rich features for estimating the likelihood of a concurrent SUD diagnosis. These first-order predictors are also conditionally dependent in their own right with second order predictors, including: diseases of the nervous systems; diseases of the ear, nose and throat; diseases of the circulatory system; diseases of the kidney and urinary tract; and other health services, among others. One can observe that in the full BBN, there are multiple non-linear relationships representing conditional dependence between variables that predict the outcome of interest.

Figure 8B:
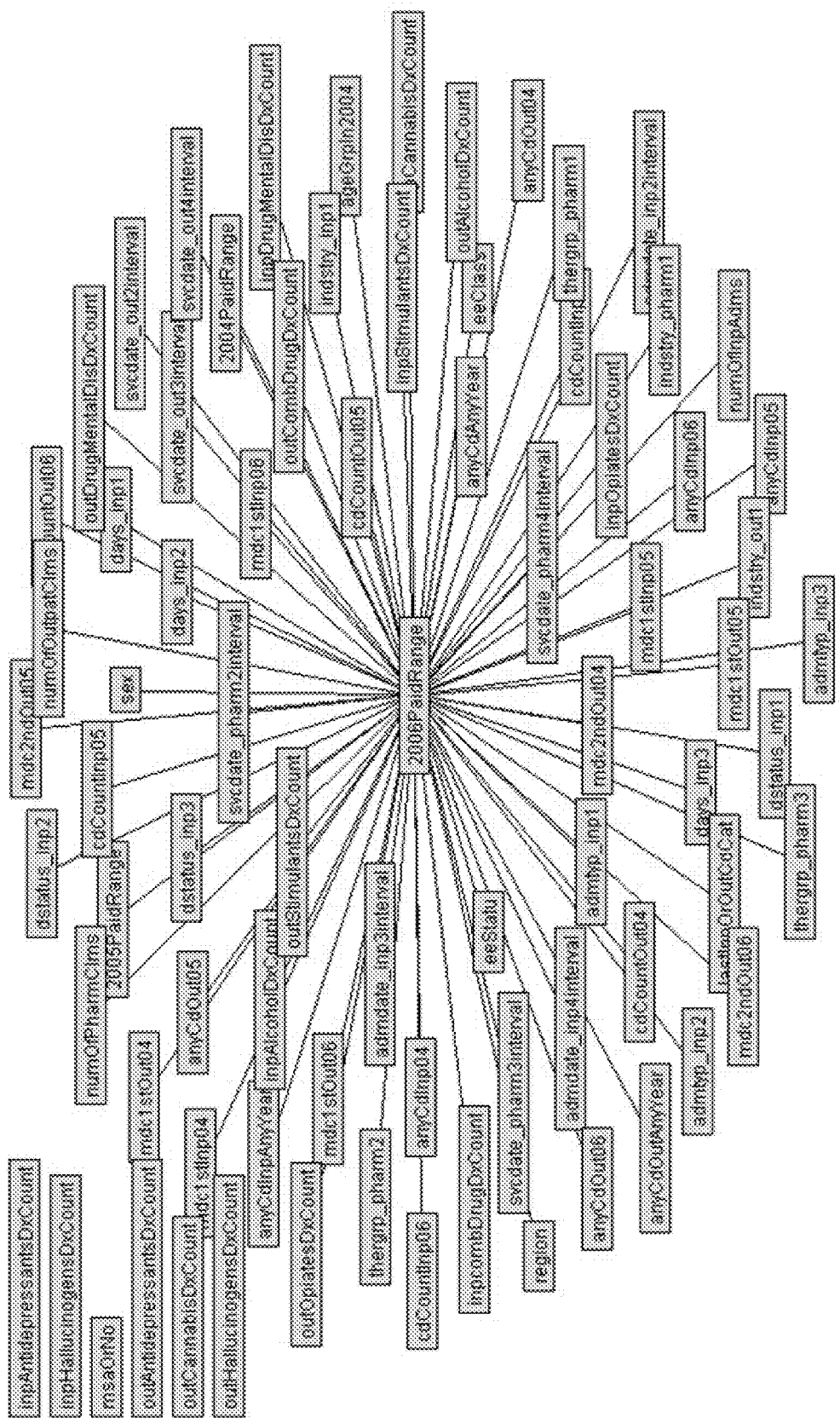
FIG. 8B is a diagram illustrating a structure of a cost model according to one embodiment of the invention.

FIG. 8B, on the other hand, details a naïve BBN classifier designed to stratify individual enrollee costs based on historical data, according to one embodiment. The naïve BBN assumes features associated with a specific dependent outcome of interest are mutually independent. It therefore provides insight into the direct information contribution of individual features. It also supports the development of quantitative contribution reports. This classifier uses available prior information to provide a specific estimate of cost range. Hence, in FIG. 8B, all of the features which share an arc (line) with the 2006 cost range outcome (2006 Paid-Range, in the center of the diagram) influence the estimate of prospective enrollee cost. Hence, all features except those excluded from the network (upper left) act as first-order predictors with varying weights according to their respective goodness of fit (strength of association) with the dependent outcome. Knowledge of demographics and claims history can be used to estimate prospective cost.

Figure 8C:
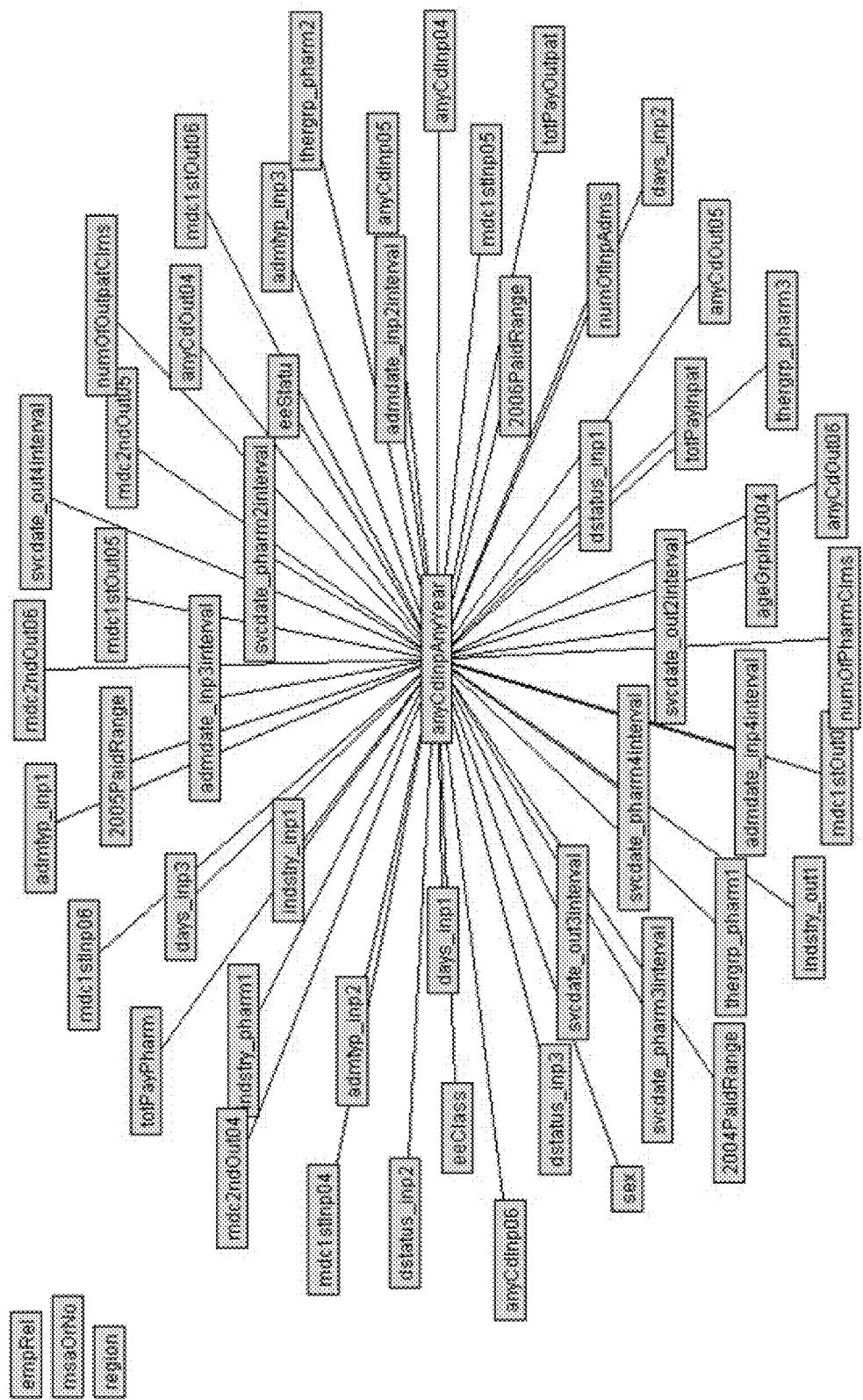

FIG. 8C details an additional naïve BBN, in this instance focused on general population screening according to one embodiment. The objective of this BBN is to use historical claims record data to develop an estimate of the probability that an enrollee has SUD, based upon the overall prevalence in our three-year study cohort. This model uses historical diagnoses, pharmacy data, enrollee demographic data, and utilization data, but rather than estimating annual cost, it estimates the likelihood of SUD within a three year enrollment period.

For each of the BBNs discussed above, according to one embodiment, certain portions (e.g., 10%) of holdout set consisting of 18,623 enrollees are used to validate the models for robustness and statistical quality. For each model, the holdout test set is input and calculated positive and negative predictive value and area-under-the-curve for each model. The tables described below detail examples of the validation results for both the screening models and the cost/treatment models.

In this embodiment, four different screening models were tested, and two screening models were identified with strong characteristics as measured by AUC. These models produced AUCs for SUD positive of 0.948 (95% Confidence Interval (CI): 0.944-0.951) and 0.736 (95% CI: 0.721-0.752), respectively, and SUD negative of 0.951 (95% CI: 0.947-0.954) and 0.738 (95% CI: 0.727-0.750), respectively. A screening model was also developed to segment enrollees positive for SUD into likely SUD category. For further validation, the holdout set and the best risk estimation model were used to assess sensitivity of detection and predictive value at different probability thresholds. To clarify, because BBNs are probabilistic, the user has the option of deciding what level of probability constitutes a positive or negative prediction. FIG. 9A shows data using optimal screening model and details sensitivity, specificity, negative and positive predictive values, as well as estimated cases detected per 100,000 enrollees and number of enrollees falsely flagged for each enrollee detected.

In addition to evaluating three-year risk detection, according to one embodiment, the use of the multi-year model was accessed to risk score enrollees on a prospective year. To do this, the hold-out set of enrollees and 2004-2005 characteristics were used to risk score enrollees for an SUD diagnosis in 2006. The enrollee population was stratified using the probability of SUD and selected ranked cohorts in sets of 50, 100, 250, and 500 in order to show how an optimal population can be selected through statistical analysis while controlling for the relative cost of false negatives and false positives. One of the challenges in identifying SUD enrollees is that the condition tends to be pervasively underdiagnosed as a result of social stigma, ethical issues, limited treatment options, and poor reimbursement. In order to try and address this effect, it is calculated sensitivity (rate of detection) and predictive value (accuracy) on both a one-year and two-year diagnosis threshold for each ranked cohort. The results are summarized in FIG. 9B. Each ranked cohort is listed individually and calculated the sensitivity (detection rate) of an SUD claim for each of 2005 and 2006 and 2005/2006 together—it is important to note that these are only claims and there may be enrollees who are clinically indicated but for whom no claims were filed. It is also calculated the Positive Predictive Value, or the probability that an enrollee flagged as a high SUD risk has had an SUD claim in 2005, 2006, or either. The optimum cohort appears to be the Top 250 group—in this group, it can successfully identify one out of three enrollees for two-year risk and of this group, and 70% of our estimates are accurate.

The holdout set was also used to evaluate the predictive power of five different BBNs to estimate next year (2006) cost based on prior years (2004 and 2005). Based upon these statistics, two of the best BBN models were selected. It has been elected to use the Naïve BBN cost model for the insights and rules because of the higher input dimensionality it supports. AUC statistics for this cost model, by cost stratification range, ranged from 0.745-0.961 (95% Confidence Interval: 0.733-0.977).

The validation analysis shows that the classifiers are robust and can be used to screen enrollees with a great degree of accuracy and estimate individual expected costs with a high degree of accuracy. To further support this analysis, the holdout set of 18,623 enrollees was used to estimate 2006 cost using 2004-2005 data while suppressing data from each enrollee's 2006 claims record. To do this, the prospective cost/utilization estimation model was applied to predict next year cost ranges. The result is a set of estimates of next year cost assuming no intervention for SUD. The estimated cost range is compared to the actual known cost range in 2006.64% of predicted cases were predicted in the correct range, and 80% of cases were within one range of accuracy.

As we move into an era of evidence-based, information driven personalized care, there is a need for tools and methods that support individualized patient intervention and management. While there has been interesting early work in these types of approaches for SUD, the results have largely been disappointing. However, there are studies which have shown that, if properly implemented, proactive targeted intervention and therapy matching can have a favorable impact on patient outcomes and costs. The current paradigm is focused on benefits limitation, broad-based disease management, and carving out behavioral health benefits. The result has been a management approach that has a "one size fits all" approach that measures performance in averages. One objective in this study was to develop a novel approach—one where sophisticated classification models are used to identify very specific enrollee sub-populations, some as small as a handful of patients, that allow one to develop highly individualized estimates of risk and benefit. As such, with validated models one can avoid enrolling patients who will receive little benefit while proactively identifying those patients who represent high potential benefit in terms of both outcomes and cost. The risk, cost and utilization models can be used to stratify patients subsequent to diagnosis into those that have the highest risk as well as the highest likelihood of successful management, a model that has already proved highly successful in the treatment and management of cancer.

Figure 10A:
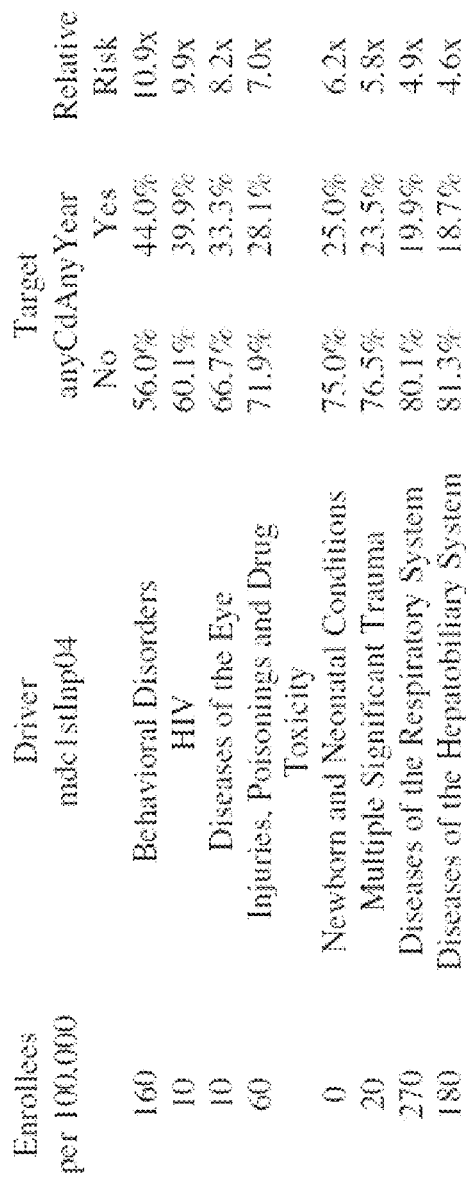
FIGS. 10A-10B are tables illustrating certain statistical results of screening models according to some embodiments of the invention.
Figure 10B:
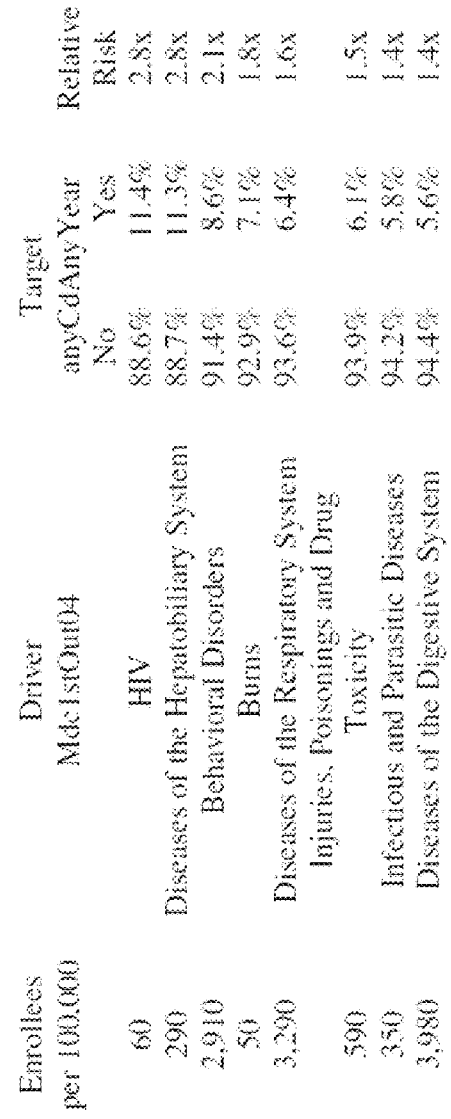

The models can be used to identify novel insights, extract rules, and develop case studies of how the models would perform when applied to a novel population. Within these populations, one can use enrollee specific historical information to calculate enrollee specific estimates of next twelve months forward costs and enrollee specific estimates of likely costs savings resulting from successful therapeutic intervention, allowing individual payors to determine the relative risks and benefits of intervention. As an example, one can estimate the relative risk of SUD based on an enrollee's inpatient and outpatient claims history. FIGS. 10A and 10B show tables that detail the relative risk of new SUD claim over the next three years based upon prior inpatient and outpatient diagnoses in 2004. These tables use only the primary ICD-9 code from the first claim in 2004, table as shown in FIG. 10A being the first inpatient claim and table as shown in FIG. 10B being the first outpatient claim, and this data is used to calculate the probability of an SUD diagnosis in the subsequent three years and corresponding relative risk. The first column also details expected prevalence based upon our study population.

The ability to estimate utilization and cost further allows individuals to detail the relative increase in expected annual cost of selected chronic diseases and trauma when an enrollee also has a diagnosis of SUD. Further, it is flagged with additional conditions, such as HIV and eye disorders, which have known associations with SUD. FIG. 16 details the expected annual cost differential, on an annual basis, for enrollees diagnosed with selected chronic conditions both with and without SUD. This illustrates, in a simple way, the manner in which a BBN can encode complex rule sets that can then be used to estimate outcomes and perform scenario modeling. In addition to looking at selected high-cost chronic diseases, several conditions are identified with relatively lower costs where SUD has a surprising cost impact. Several of these relationships have already been identified in the literature in terms of the relationship to cost, utilization and outcomes in respiratory disease, trauma, and infectious disease. Note that these estimates include only cost estimation derived from diagnosis, and do not include many of the other factors such included in our models such as historic pharmacy utilization, frequency of outpatient utilization, and demographics, which further impact expected cost however have been omitted in order to save space.

Multiple known factors can be combined in the model to produce combined estimates of risk and cost. In one embodiment, and enrollee's historical outpatient utilization of pharmacy and outpatient diagnoses can be used to calculate probability of diagnosis and relative risk: in one example CNS drugs and an outpatient diagnosis of diseases of the hepatobiliary system and pancreas are used to calculate the risk of SUD—in this instance, 31.3%, or a 7.8× relative risk compared to the overall population.

The cost models can then be used to estimate the expected cost distribution of the enrollee with and without SUD. FIG. 11A shows a table that details expected next year cost distribution without SUD, while FIG. 11B shows a table that details the expected next year cost distribution of an identical case with SUD: the case has a pancreatic disorder and is using some type of CNS drug. Without SUD, the annual cost of this enrollee is expected to be above $10,000 only 43.6 o the time. With SUD, the annual cost of this enrollee is expected to exceed $10,000 73.3% of the time.

As a further analysis, the validated cost model was used to estimate the potential savings attributable to intervention. It was sought to estimate the reduction in 2006 total enrollee cost if enrollees with SUD were successfully treated at the end of 2005, making the assumption that successful disease management of SUD would change utilization patterns. Accordingly variables were suppressed that describe utilization in 2004 and 2005 and all variables related to 2006 utilization were also suppressed, and the estimated cost distributions of all 18,623 enrollee cases in the holdout set were compared between those who had SUD and identical matched cases without SUD. Using the analysis above, an estimated hypothetical 2006 post-treatment cost for each enrollee was calculated and compared to the actual known 2006 cost for each enrollee to calculate an estimated savings. The entire cohort was ranked by SUD risk score and then within each scoring group ranked by estimated savings. Average per-enrollee savings was calculated for top fractional cohorts in the holdout set consisting of top-ranked cohorts of 50, 100, 250, and 500 enrollees. Estimated savings by cohort were calculated as follows; top 50 enrollee cohorts, average savings $23,284 per enrollee; top 100 enrollee cohorts, average savings $12,317 per enrollee; top 250 enrollee cohorts, average savings $4,927 per enrollee; top 500 enrollee cohort, average savings $2,463 per enrollee.

This analysis indicates, for example, that selecting the Top 500 enrollees (out of our 18,623 enrollee test set) produces an expected cost reduction benefit of approximately $2,500 in annual savings. Restricting the set to the Top 250 cases produces an expected savings of approximately $5,000 per enrollee, and by further restricting our interventional population to the Top 100 enrollees, we increase our expected average reduction to over $12,000 per patient. Using this approach, one can stratify an interventional population and tune the marginal benefit to maximize both enrollee benefit and financial return in light of the costs and success rate of a given intervention. The actual return on intervention is highly dependent on the individual payor and treatment modality, as the cost and success rate of interventions varies greatly, from as much as $30,000 per month at the Betty Ford Clinic to as little $300 per month for outpatient programs or $147 per month for clinic based methadone treatment. These cost estimates need to be further adjusted based on expected success and recidivism rates, as these rates can vary significantly. While payors need to make informed policy and medical decisions regarding treatment recommendations and reimbursement, with accurate validated stratification tools, payors can make significantly more informed decisions in the context of overall utilization benefit relative to intervention.

One of the interesting phenomena in the stratification exercise was that the expected enrollee savings did not necessarily appear to scale with general utilization. Many patients in lower utilization categories appeared to score higher expected savings than patients in higher utilization categories. This led to examine specific cases in the model to attempt to understand why this phenomenon occurred. For example, for enrollees with cancer necessitating inpatient care, 90.1% of SUD negative enrollees cost over $10,000 in 2006, while 97.3% of SUD positive enrollees cost over $10,000 in 2006. In contrast, for enrollees with respiratory disorders necessitating inpatient care in 2006, 78.3% of SUD negative enrollees cost over $10,000 in 2006, while 90.4% of SUD positive enrollees cost over $10,000 in 2006. SUD status in cancer enrollees results in a 7.3% difference in expected cost category, while difference in status for respiratory enrollees yields a 12.1% difference in costs. As other factors are added, such as medication history, one can develop a rich picture of enrollee segments where SUD is impacting annual cost. The difference between these enrollee populations is that SUD appears to impact long-term chronic condition more heavily than short term acute conditions. A reasonable hypothesis for this difference is that in conditions where patient compliance and effective pharmacy management are critical to disease management, SUD may negatively impact compliance and significantly increase outpatient and inpatient resource utilization.

Assuming a payor has interventional strategies that will generate sufficient response at cost levels appropriate relative to estimated savings, this method can be implemented as a near-real-time decision support system. Enrollee data can be fed into the costing and screening models to develop stratified estimates of cost and risk.

At this point, the greatest challenge in implementation is not a technical, but rather a policy challenge. In addition to issues of intervention costs and success rates which may produce widely varying returns for different populations and payors, there is a need to account for concerns regarding patient privacy, potential stigma, and potential issue with regard to access to care. One can address this dilemma to some degree through selected referral rules and thresholds that severely reduce false positives, while weighing the societal costs of failing to intervene. For example, one could treat all enrollees, and ensure that it reaches all SUD enrollees, but at the cost of providing unnecessary clinical evaluations to 96% of enrollees (assuming 4% natural prevalence), both wasting resources and potentially stigmatizing these enrollees. Alternatively, one could only clinically evaluate the highest risk enrollee, and would be certain to avoid unnecessary evaluation and treatment, but would only help one enrollee. So it must identify a threshold between these two points. The appropriate selection of thresholds for referral and intervention needs to be carefully considered in the context of medical ethics and competing priorities and resources. However, the ability to use accurate stratification technologies has to potential to significantly improve cost management and the delivery of care relative to the current "blunt" paradigm of benefits limitation for controlling behavioral health costs.

Using this method, one can develop forward-looking stratified individual estimates of disease risk for each enrollee in our selected population. This estimate takes into effect utilization histories, co-morbidities, chronic conditions, demographic data, and pharmacy data of each enrollee. Importantly, it should be focused on data that are available currently and do not require complex or expensive collection mechanisms to be developed. Further, within this complex matrix, 12-month forward total cost can be estimated for the enrollee with SUD and assuming the enrollee is SUD-free. This allows individuals to then rank all of the selected enrollees by both i) total estimated forward 12-month cost, and ii) total estimated forward 12-month cost savings attributable to treatment exclusive of treatment costs. These tools should allow payors and providers to make more informed and thoughtful decisions with respect to referral for treatment in the context of available resources and ethical decision making.

A large, heterogeneous population of commercial enrollees can be successfully modeled, applying state-of-the-art machine learning technology to develop complex and accurate multivariate models that support near-real time scoring of novel payor populations based on historic claims and diagnostic models. The initial validation results indicate that one can stratify enrollees with SUD diagnoses with a high degree of sensitivity and specificity.

In the screening model series, it is focused on a selection of variables and model types that the support the use of a priori (known at or before the time of diagnosis) variables to predict a subsequent diagnosis of SUD. An embodiment of the invention involved documentation of the screening model set and consists of the following documentation components: i) Data Preparation—discussion of additional data preparation; ii) Models—succinct description of the models; iii) Validation—validation statistics of the final models; iv) Structures—succinct overview of the model structures; v) Prevalence—Prevalence and Incidence of CD; vi) Significant Factor Rankings—Rankings of factors by significance; vii) Clusters of Interest—Interesting Patterns in the data; viii) Selected Summary Tables—Tables detailing expanded rules; and ix) Combined Rules/Insights—How different factors interact to create outcomes.

These screening models include only those enrollees present from enrollment in 2004 through 2006, totaling 185,322. This is done to focus on relationships affecting longitudinal admissions and treatment cost and not on whatever other effect (such as changing insurance coverage or employment) explains the decrease in database participation. As noted in earlier reports, Thomson provided data for the years 2004, 2005, and 2006. Data shows that there were 400,000 enrollees for 2004, but participation declines to 304,496 in 2005 and 185,322 in 2006. For the models described here, we used 90% of this as a training set and withheld the remaining 10% for validation. The records modeled totaled 166,699 enrollees.

A combination of IDC-9-CM diagnosis codes is utilized such as those in Sections 660—Alcohol-related disorders, 661—Substance-related disorders, and 663—Screening and history of mental health and substance abuse. These codes were further grouped to improve model robustness and statistical power. Major Diagnostic Category codes were also used.

For the screening model, in one embodiment, five models were created which support a multi-metric disease screening approach. Essentially, each model provides subtly different information on the probability of disease. Each model used a different combination of data preparation, complexity inflator/deflator, and specified structure to represent the structure of the data differently. Each BBN was tested and validated separately in order to determine the most robust classifier.

Within the context of these models, the contribution levels of the independent variables in the naïve models are tanked and then ranked quantitatively by MDL score. While a number of these variables, such as an earlier substance abuse diagnosis, are not useful in a novel population and some, such as current year payments, are post-facto variables, many, such as prior year payment ranges, therapeutic group, and previous outpatient admissions, are useful. As an example, the type of first inpatient admission had the highest score in estimating an inpatient diagnosis of SUD, the second highest score was the historical number of inpatient admissions.

In addition to the MDL contribution scores, according to one embodiment, it is also analyzed expected change in distribution by population to score variables on their degree of change by population. This is a subtly different analysis which allows individuals to see which variables change the most when the dependent variable changes. Whereas the MDL contribution analysis scores the individual feature by its contribution to model predictive power by goodness of fit, the Mean Integer Value (MIV) change scoring methodology ranks variables by the degree to which an outcome changes—hence it is a metric of severity of impact on predicted outcome. As an example of MIV influence, the discharge status of the first inpatient admission had the highest score in estimating an inpatient diagnosis of SUD, the second highest score was the historical number of inpatient admissions.

Using the Full Bayes networks, a few selected conditional dependence clusters of interest can be examined. In the Full Bayes Inpatient model as shown in FIG. 8A, a diagnosis of CD is predicted by various major diagnostic categories for historic encounters. Applying the ranked variable contributions and using the clusters of interest, a serious of inference tables can be developed which calculate the probability of a diagnosis of substance abuse in 2006 based on a priori variables. The table as shown in FIG. 12 details the relative risk by therapeutic group for first prescription. If those therapeutic groups for which there is limited evidence were ignored, it can be seen that the groups Smooth Muscle Relaxants (27), Immunosuppressants (21), Pharmaceutical Aids/Adjuvants (31), CNS (8), Gastrointestinal (17), Heavy Metal Antagonists (17), Blood Form/Coag (6), Autonomic Drugs (4), and Unclassified (29) agents provide significant increases in risk.

In the table as shown in FIG. 13, the Full Bayes Classifier is used to identify those diagnoses most likely to be associated with the first inpatient admission in the enrollee claims record: Diagnoses 19 (Mental Diseases and Disorders) and 20 (Alcohol/Drug Use and Alcohol/Drug Induced Organic Mental Disorders) are obviously associated with this type of admission, but examining the following diagnoses provide additional insight into the type of conditions that are occurring concurrent with substance abuse. Based on FIG. 13, the following diagnoses appear to co-occur with an admission related to substance abuse: i) Newborns and Other Neonates with Conditions Originating in Perinatal Period (MDC 15); ii) Burns (MDC 22); iii) Human Immunodeficiency Virus Infections (25); iv) Diseases and Disorders of the Eye (2); v) Multiple Significant Trauma (24); vi) Myeloproliferative Diseases and Disorders, Poorly Differentiated Neoplasm (17); and vii) Diseases and Disorders of the Blood, Blood Forming Organs, Immunological Disorders (16).

The scenarios below detail selected instances of how the features of the model interact to produce specific estimates of CD. Using the Naïve Inpatient or Outpatient screening model, according to one embodiment, a series of scenarios to identify high risk patients can be developed. For example, we can develop thousands of pharmacy benefit sequences that provide an estimate of relative risk, a few example scenarios just using primary and secondary scripts follow: CNS/CNS (2.9× relative risk), Expectorant/CNS (2.1× relative risk), CNS/Gastro (2.1× relative risk).

In one embodiment of the invention, initial outpatient diagnosis in the context of employment industry was examined. In one example, it was determined that the employment category of Durable Goods Manufacturing had the highest relative risk of diagnosis: 2.9×.

In one embodiment of the invention which represents the inherent complexity of this classification problem, we created a more complex case: an enrollee in Durable Goods Manufacturing is combined with either an HIV or Liver/Pancreas outpatient diagnosis, which increases relative risk to 3.2×. If we further add in an Autonomic Drug script, the relative risk increases to 4.3× and the probability of SUD to 17.5%. Shifting the same case to an inpatient, as opposed to an outpatient, diagnosis increases relative risk to 18.5× and probability of SUD diagnosis to 74.7%.

In one embodiment of the invention, a selection of variables and model types were developed to the support the use of a priori (known at or before the time of diagnosis) variables to estimate future utilization and cost of a specific enrollee. An embodiment of the invention involved documentation of the cost model set and consists of the following documentation components: i) Data Preparation—discussion of additional data preparation; ii) Models—succinct description of the models; iii) Validation—validation statistics of the final models; iv) Structures—succinct overview of the model structures; v) Prevalence—Prevalence and Incidence of CD; vi) Significant Factor Rankings—Rankings of factors by significance; vii) Clusters of Interest—Interesting Patterns in the data; viii) Selected Summary Tables—Tables detailing expanded rules; and ix) Combined Rules/Insights—How different factors interact to create outcomes.

These models include only those enrollees present from enrollment in 2004 through 2006, totaling 185,322. This was done to focus on relationships affecting longitudinal admissions and treatment cost and not on whatever other effect (such as changing insurance coverage or employment) explains the decrease in database participation. As noted in earlier reports, Thomson provided data for the years 2004, 2005, and 2006. Data shows that there were 400,000 enrollees for 2004, but participation declines to 304,496 in 2005 and 185,322 in 2006. For the models described here, we used 90% of this as a training set and withheld the remaining 10% for validation. The records modeled totaled 166,699 enrollees.

Enrollee utilization and cost data were organized into ranges. Utilization rates (frequency counts of service utilization) were parameterized into reference ranges using equal area binning, wherein the ranges were set to have equal frequency counts for all ranges in a given feature. Cost data were organized into specific cost ranges intended to have utility to payors, but could be organized differently based upon user specification.

For the cost model, in one embodiment, six models were created which support a multi-metric disease screening approach. Essentially, each model provides subtly different information on the probability of disease. Each model used a different combination of data preparation, complexity inflator/deflator, and specified structure to represent the structure of the data differently. Each BBN was tested and validated separately in order to determine the most robust classifier.

The above models were validated using inter-set validation. A 10% holdback set consisting of 18,623 records was used to validate the models for the robustness of their ability to stratify prospective enrollee utilization rates and costs into appropriate ranges.

Within the context of these models, the contribution levels of the independent variables were ranked in the naïve models and then ranked quantitatively by MDL score in the Demographics, Diagnoses and Cost and in the Inpatient and CD-Only variants of these models. The highest contributor to cost estimation is total frequency of outpatient claims, the second highest total frequency of pharmacy claims, third highest is enrollee cost in the prior year.

While a number of these variables, such as an earlier substance abuse diagnosis, are not useful in a novel population and some, such as current year payments, are post-facto variables, many, such as prior year payment ranges, therapeutic group, and previous outpatient admissions, are useful. The Selected Summary Tables section discusses the specific interpretations of these variables in more detail.

In addition to the MDL contribution scores of the Naïve model, the expected change is also analyzed in distribution by population to score variables on their degree of change by population. This is a subtly different analysis which allows us to see which variables change the most when the dependent variable changes (in this instance 2006 Paid Range). Whereas the MDL contribution analysis scores the individual feature by its contribution to model predictive power by goodness of fit, the MIV change scoring methodology ranks variables by the degree to which an outcome changes—hence it is a metric of severity of impact on predicted outcome.

In the naïve cost model, the top three associated features scored by MIV change are the first inpatient diagnosis group in the current year and the admission type and discharge status associated with the first inpatient claim in the enrollee claims record.

Figure 14A:
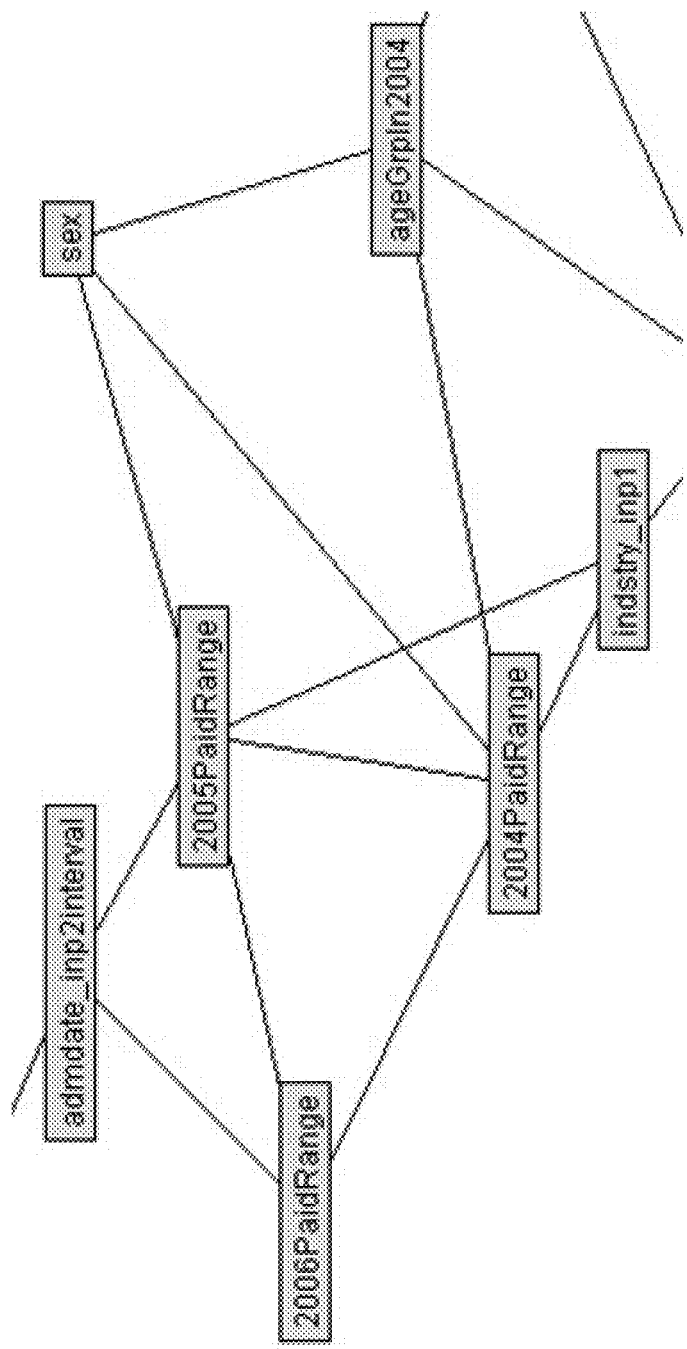
FIGS. 14A-14D show clusters of interest of structures of certain cost models according to some embodiments of the invention.
Figure 14B:
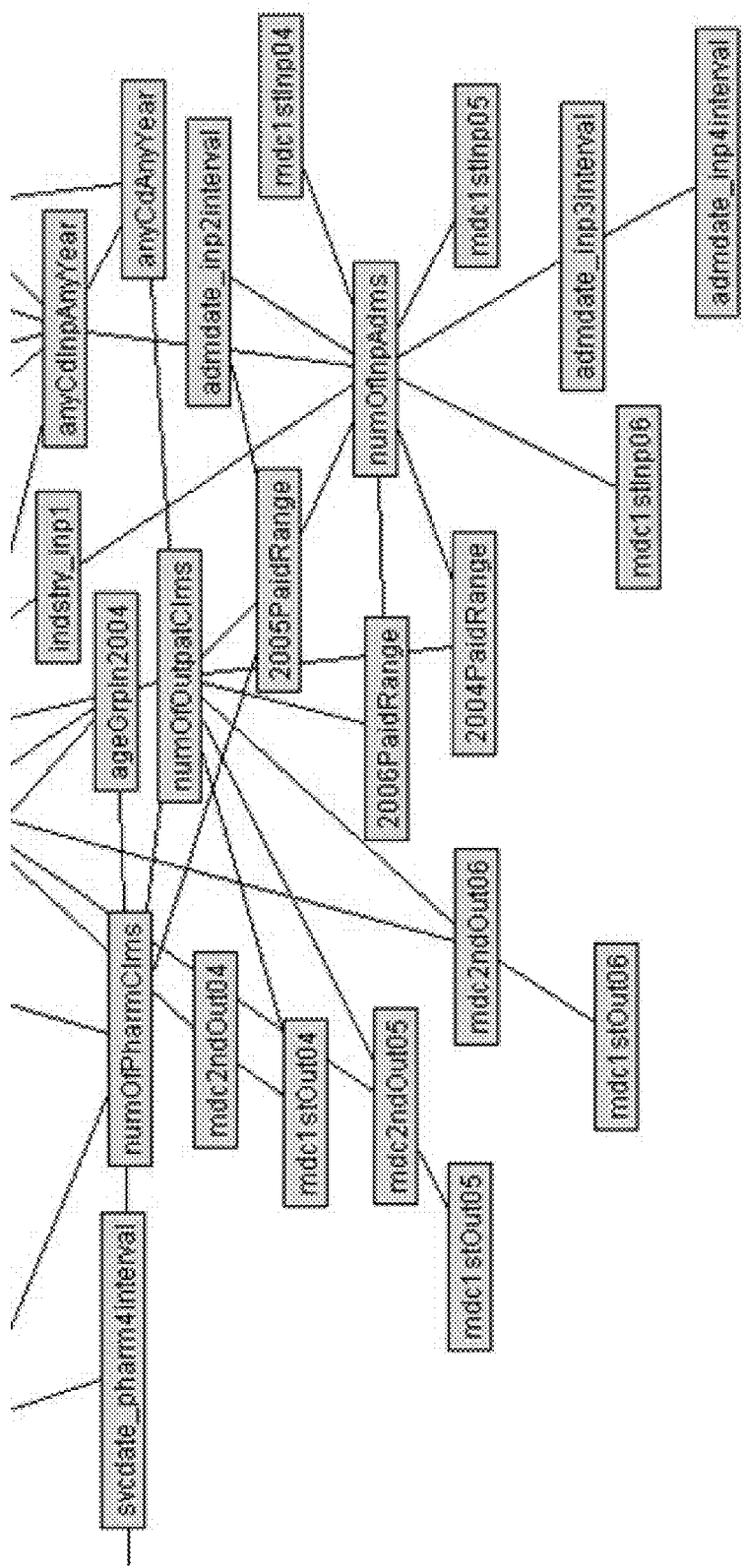
Figure 14C:
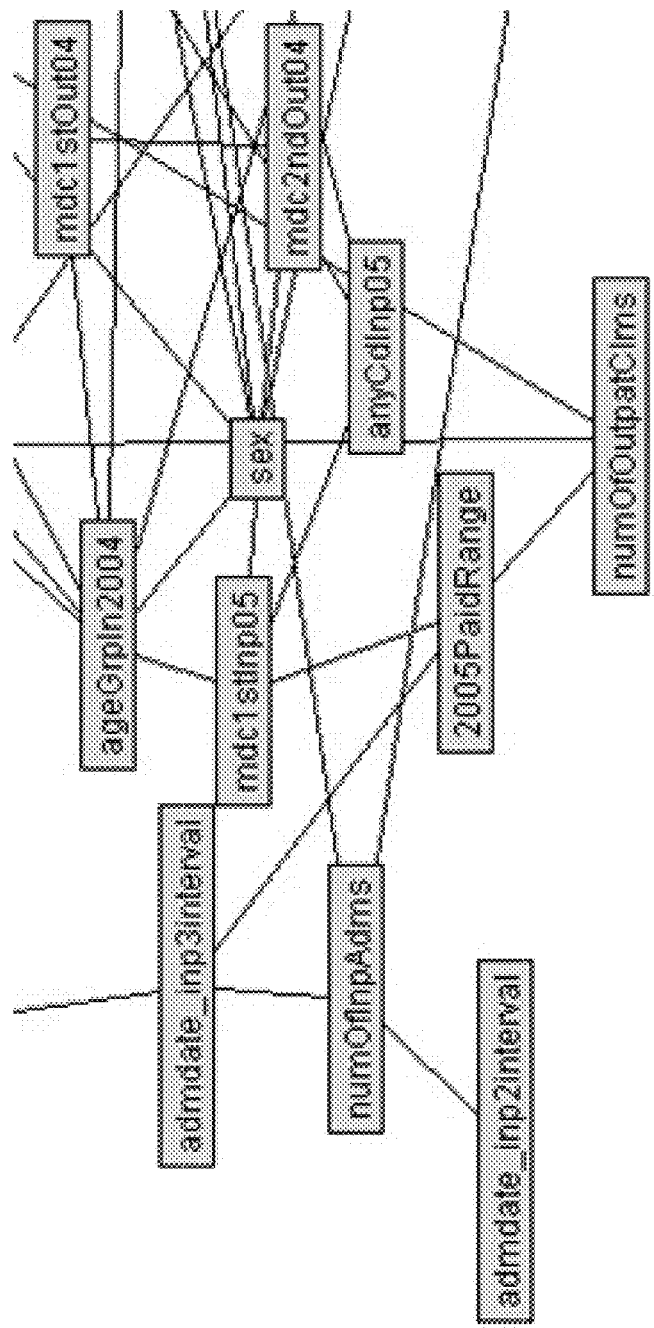
Figure 14D:
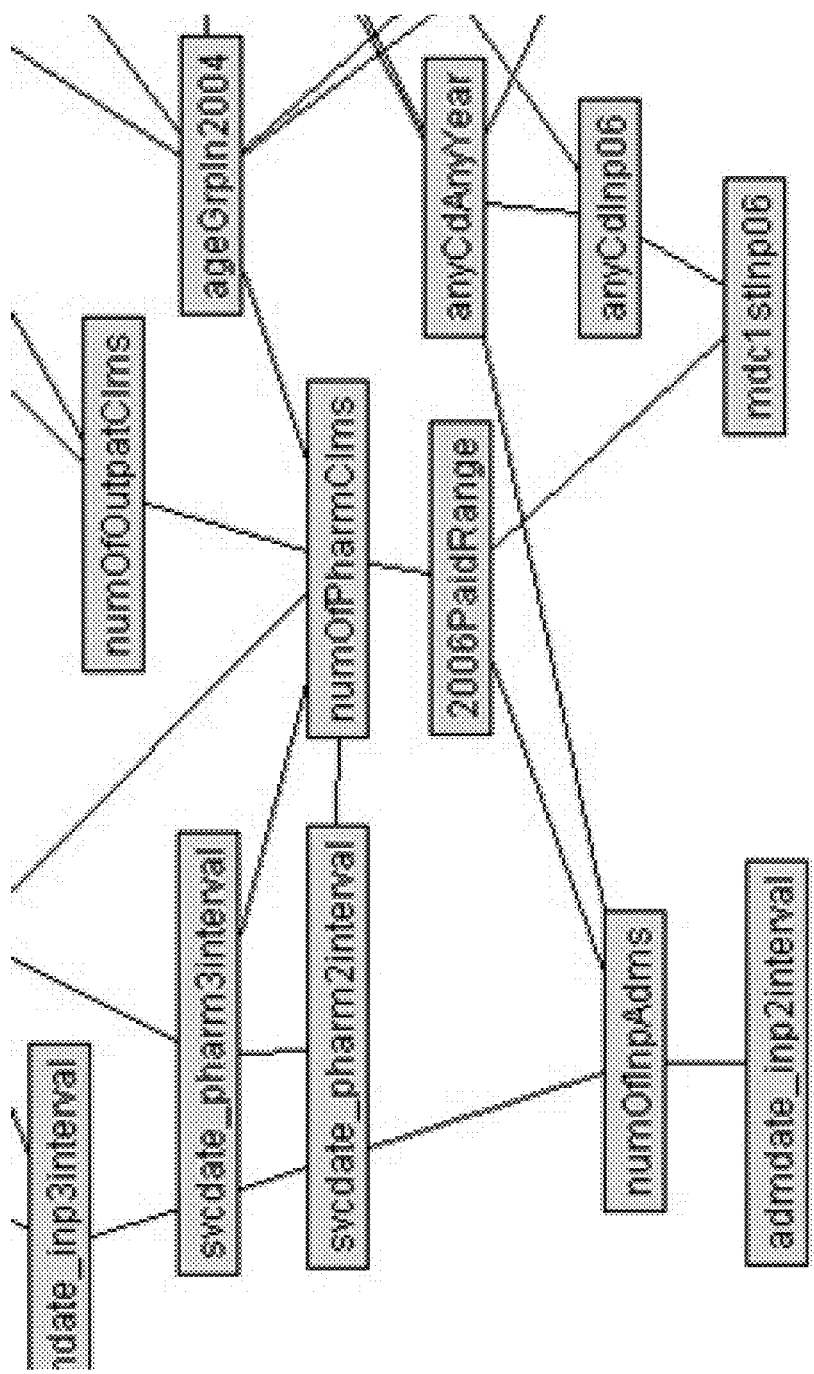

In examining each model, according to one embodiment, factors of structure can be identified which help to think about the importance of factors in scoring patients for cost. In the demographics only model as shown in FIG. 14A, it can be observed that the paid ranges are related to each other, but outside the cluster the group is related to sex, age, industry, and admission interval. In the broad population model as shown in FIG. 14B, it can be observed that the cost is a function of inpatient utilization, outpatient utilization, and admission interval and the utilization is driven by age, industry, diagnostic categories, admission interval, whether or not the enrollee has a diagnosis of CD at any time. The 2005 paid range is a function of pharmacy, inpatient, and outpatient utilization and first inpatient diagnostic category as shown in FIG. 14C. The 2004 paid range is a function of first inpatient diagnostic category as shown in FIG. 14D. In the CD-only population, it can be observed that each year's cost is a function of utilization and when the CD diagnosis occurs. There are relationships between type of diagnosis and frequency of co-occurring diagnoses Using the naive population cost stratification model, we calculated a relative outpatient cost ranking by diagnostic category as shown in FIG. 15A. Using the naive cost stratification model, a relative inpatient cost ranking can be calculated by diagnostic category as shown in FIG. 15B. FIG. 15A shows that that CD is actually one of the more expensive outpatient diagnoses, with CD ranking as the fifth most expensive outpatient diagnosis in terms of ramifications on utilization and annual cost. In the Inpatient population, it is one of the least expensive disorders, however when adjusted for frequency, its costs contribution is about middle of the pack. Within CD the population, we stratified the cost by sub-diagnosis.

Further, FIG. 16 details the relative increase in expected annual cost of selected chronic diseases and trauma when a patient also has a diagnosis of CD. Further, we have flagged additional conditions, such as HIV and Eye disorders, that also seem to have a strong association with CD.

Figure 17:
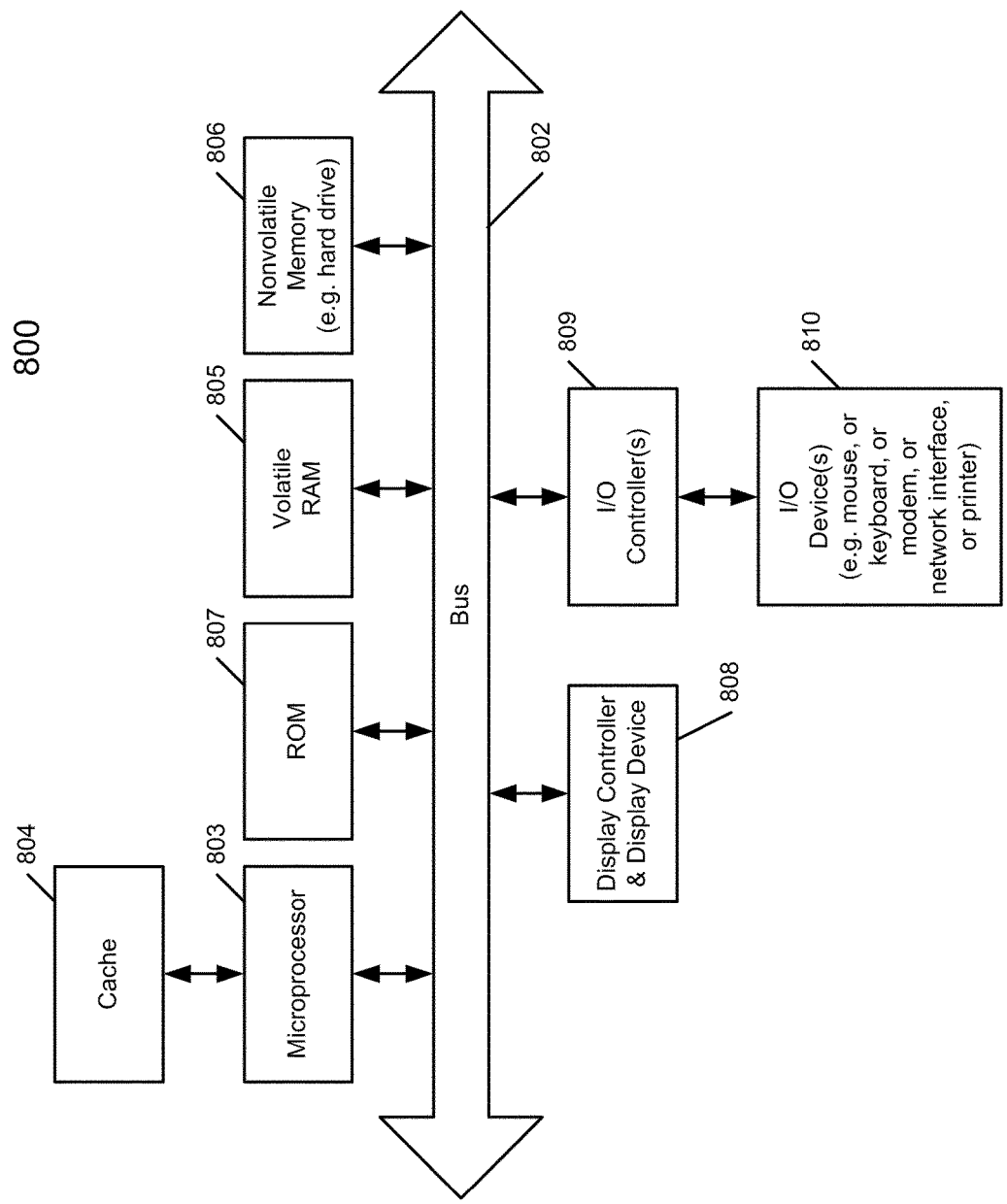
FIG. 17 is a block diagram of a data processing system, which may be used with one embodiment of the invention.

FIG. 17 is a block diagram of a data processing system, which may be used with one embodiment of the invention. For example, the system 800 shown in FIG. 17 may be used as a client and/or a server of FIG. 1. Note that while FIG. 17 illustrates various components of a computer system, it is not intended to represent any particular architecture or manner of interconnecting the components; as such details are not germane to the present invention. It will also be appreciated that network computers, handheld computers, cell phones and other data processing systems which have fewer components or perhaps more components may also be used with the present invention. The computer system of FIG. 17 may, for example, be an Apple Macintosh computer or MacBook, or an IBM compatible PC.

As shown in FIG. 17, the computer system 800, which is a form of a data processing system, includes a bus or interconnect 802 which is coupled to one or more microprocessors 803 and a ROM 807, a volatile RAM 805, and a non-volatile memory 806. The microprocessor 803 is coupled to cache memory 804. The bus 802 interconnects these various components together and also interconnects these components 803, 807, 805, and 806 to a display controller and display device 808, as well as to input/output (I/O) devices 810, which may be mice, keyboards, modems, network interfaces, printers, and other devices which are well-known in the art.

Typically, the input/output devices 810 are coupled to the system through input/output controllers 809. The volatile RAM 805 is typically implemented as dynamic RAM (DRAM) which requires power continuously in order to refresh or maintain the data in the memory. The non-volatile memory 806 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 17 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 802 may include one or more buses connected to each other through various bridges, controllers, and/or adapters, as is well-known in the art. In one embodiment, the I/O controller 809 includes a USB (Universal Serial Bus) adapter for controlling USB peripherals. Alternatively, I/O controller 809 may include an IEEE-1394 adapter, also known as FireWire adapter, for controlling FireWire devices.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments of the invention also relate to an apparatus for performing the operations herein. Such a computer program is stored in a non-transitory computer readable medium. A machine-readable medium includes any mechanism for storing information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices).

The processes or methods depicted in the preceding figures may be performed by processing logic that comprises hardware (e.g. circuitry, dedicated logic, etc.), software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

Embodiments of the present invention are not described with reference to any particular programming language. It will be appreciated that a variety of programming languages may be used to implement the teachings of embodiments of the invention as described herein.

In the foregoing specification, embodiments of the invention have been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A computer-implemented method for evaluating enrollees of a health insurance plan, the method comprising:
   receiving, by a training module executed within a server, a first set of health insurance claim data for a first group of individuals from a client device over a network, the first group of individuals representing enrollees of one or more first health insurance plans and the first set of health insurance claim data representing historic insurance claim information for each individual in the first group of individuals, wherein the first set of historic insurance claim information includes co-morbid conditions;
   separating, by the training module, the received first set of health insurance claim data into a training set of claim data and a holdout set of claim data;
   creating, by the training module, a set of Bayesian belief network (BBN) model candidates, wherein creating the set of BBN model candidates comprises:
   a) calculating distributions of discrete states for variables of the BBN network,
   b) generating a first BBN model by performing a preliminary modeling operation on the variables to identify appropriate machine learning parameters,
   c) generating a second BBN model by performing a global modeling operation to set the appropriate machine learning parameters and to observe variable relationships,
   d) generating a third BBN model by performing a naïve modeling operation to identify a contribution of each of the variables, and
   e) generating a fourth BBN model by performing a focused modeling operation on a subset of the variables identified in at least one of the preliminary modeling operation, the global modeling operation, and the naïve model operation, wherein the set of BBN model candidates comprises at least the first BBN model, the second BBN model, the third BBN model, and the fourth BBN model;

assigning, by the training module, a score to each BBN model candidate of the set of BBN model candidates using a predetermined scoring method;

selecting, by the training module, a BBN model from the set of BBN model candidates, the selected BBN model having the highest score among the set of BBN model candidates, wherein the selected BBN model is a screening BBN model to identify individuals having risk characteristics associated with a disorder or a cost BBN model to produce cost estimates with and without intervention or treatment of the disorder;

validating, by the training module, the selected BBN model using the holdout set of claim data by generating a receiver operating characteristic (ROC) curve based on an outcome of the selected BBN model operated on the holdout set of claim data, and calculating an area under the curve (AUC) based on the ROC curve to evaluate predictive correctness of the selected BBN model given the holdout set of claim data;

receiving, by a diagnostic module executed within the server, a second set of health insurance claim data for a second group of individuals from the client device over the network, the second group of individuals representing enrollees of one or more second health insurance plans;

identifying, by the diagnostic module, a subset of individuals in the second group of individuals having the risk characteristics associated with the disorder by performing a screening operation on the received second set of health insurance claim data using the screening BBN model;

generating a health insurance policy for one or more individuals in the identified subset of individuals, wherein the health insurance policy is based on the screening operation; and transmitting the health insurance policy to the client device over the network.

2. The method of claim 1, wherein the first set of historic insurance claim information includes at least two of the group consisting of: hospitalizations, outpatient services, procedure codes, diagnostic codes, diagnostic-related group codes, drug prescribed, chronic conditions, an interval between encounters, historic cost and utilization trends, enrollee industry, employment status, sex, age, region of country, and urban or rural setting.

3. The method of claim 1, wherein the predetermined scoring method comprises a minimum description length (MDL) method.

4. The method of claim 1, further comprising retraining the screening BBN model and the cost BBN model based on the second set of health insurance claim data and the cost estimates for future use.

5. A non-transitory computer-readable storage medium having computer instructions stored therein, which when executed by a computer, cause the computer to perform a method for evaluating enrollees of a health insurance plan, the method comprising:

receiving, from a client device over a network, a first set of health insurance claim data for a first group of individuals, the first group of individuals representing enrollees of one or more first health insurance plans and the first set of health insurance claim data representing historic insurance claim information for each individual in the first group of individuals, wherein the first set of historic insurance claim information includes co-morbid conditions;

separating the received first set of health insurance claim data into a training set of claim data and a holdout set of claim data;

creating a set of Bayesian belief network (BBN) model candidates, wherein creating the set of BBN model candidates comprises:

a) calculating distributions of discrete states for variables of the BBN network, b) generating a first BBN model by performing a preliminary modeling operation on the variables to identify appropriate machine learning parameters, c) generating a second BBN model by performing a global modeling operation to set the appropriate machine learning parameters and to observe variable relationships, d) generating a third BBN model by performing a naïve modeling operation to identify a contribution of each of the variables, and e) generating a fourth BBN model by performing a focused modeling operation on a subset of the variables identified in at least one of the preliminary modeling operation, the global modeling operation, and the naïve model operation, wherein the set of BBN model candidates comprises at least the first BBN model, the second BBN model, the third BBN model, and the fourth BBN model;

assigning a score to each BBN model candidate of the set of BBN model candidates using a predetermined scoring method;

selecting a BBN model from the set of BBN model candidates, the selected BBN model having the highest score among the set of BBN model candidates, wherein the selected BBN model is a screening BBN model to identify individuals having risk characteristics associated with a disorder or a cost BBN model to produce cost estimates with and without intervention or treatment of the disorder;

validating the selected BBN model using the holdout set of claim data by generating a receiver operating characteristic (ROC) curve based on an outcome of the selected BBN model operated on the holdout set of claim data, and calculating an area under the curve (AUC) based on the ROC curve to evaluate predictive correctness of the selected BBN model given the holdout set of claim data;

receiving a second set of health insurance claim data for a second group of individuals from the client device over the network, the second group of individuals representing enrollees of one or more second health insurance plans;

identifying a subset of individuals in the second group having the risk characteristics associated with the disorder by performing a screening operation on the received second set of health insurance claim data using the screening BBN model;

generating a health insurance policy for one or more individuals in the identified subset of individuals, wherein the health insurance policy is based on the screening operation; and transmitting the health insurance policy to the client device over the network.

6. The computer-readable storage medium of claim 5, wherein the first set of historic insurance claim information includes at least two of the group consisting of: hospitalizations, outpatient services, procedure codes, diagnostic codes, diagnostic-related group codes, drug prescribed, chronic conditions, an interval between encounters, historic cost and utilization trends, enrollee industry, employment status, sex, age, region of country, and urban or rural setting.

7. The computer-readable storage medium of claim 5, wherein the predetermined scoring method comprises a minimum description length (MDL) method.

8. The computer-readable storage medium of claim 5, wherein the method further comprises retraining the screening BBN model and the cost BBN model based on the second set of health insurance claim data and the cost estimates for future use.

9. A data processing system, comprising:
   a processor; and
   a memory coupled to the processor to store instructions, which when executed from the memory, cause the processor to:
      receive a first set of health insurance claim data for a first group of individuals from a client device over a network, the first group of individuals representing enrollees of one or more first health insurance plans and the first set of health insurance claim data representing historic insurance claim information for each individual in the first group of individuals, wherein the first set of historic insurance claim information includes co-morbid conditions;
      separate the received first set of health insurance claim data into a training set of claim data and a holdout set of claim data; create a set of Bayesian belief network (BBN) model candidates, by:
         a) calculating distributions of discrete states for variables of the BBN network,
         b) generating a first BBN model by performing a preliminary modeling operation on the variables to identify appropriate machine learning parameters,
         c) generating a second BBN model by performing a global modeling operation to set the appropriate machine learning parameters and to observe variable relationships,
         d) generating a third BBN model by performing a naïve modeling operation to identify a contribution of each of the variables, and
         e) generating a fourth BBN model by performing a focused modeling operation on a subset of the variables identified in at least one of the preliminary modeling operation, the global modeling operation, and the naïve model operation,
      wherein the set of BBN model candidates comprises at least the first BBN model, the second BBN model, the third BBN model, and the fourth BBN model;
      assign a score to each BBN model candidate of the set of BBN model candidates using a predetermined scoring method,
      select a BBN model from the set of BBN model candidates, the selected BBN model having the highest score among the set of BBN model candidates, wherein the selected BBN model is a screening BBN model to identify individuals having risk characteristics associated with a disorder or a cost BBN model to produce cost estimates with and without intervention or treatment of the disorder,
      validate the selected BBN model using the holdout set of claim data by generating a receiver operating characteristic (ROC) curve based on an outcome of the selected BBN model operated on the holdout set of claim data, and calculating an area under the curve (AUC) based on the ROC curve to evaluate predictive correctness of the selected BBN model given the holdout set of claim data;
      receive a second set of health insurance claim data for a second group of individuals from the client device over the network, the second group of individuals representing enrollees of one or more second health insurance plans;
      identify a subset of individuals in the second group of individuals having the risk characteristics associated with the disorder by performing a screening operation on the received second set of health insurance claim data using the screening BBN model;
      generate a health insurance policy for one or more individuals in the identified subset of individuals, wherein the health insurance policy is based on the screening operation; and
      transmit the health insurance policy to the client device over the network.

10. The system of claim 9, wherein the processor is further configured to retrain the screening BBN model and the cost BBN model based on the first second set of health insurance claim data and the cost estimates for future use.

11. The system of claim 9, wherein the processor is further configured to train the screening BBN model and the cost BBN model prior to receiving the first set of health insurance claim data.

12. The method of claim 1, wherein the method further comprises retraining the screening BBN model and the cost BBN model based on the first set of health insurance claim data and the enrollee-specific cost estimates for future use.

13. The method of claim 1, wherein the method further comprises training the screening BBN model and the cost BBN model prior to receiving the first set of health insurance claim data.

14. The method of claim 1, further comprising using the selected BBN model to develop enrollee-specific estimates of disease risk, enrollee-specific future estimates of utilization and cost, and enrollee-specific estimates of a change which would result from intervention or treatment.

15. The method of claim 1, wherein the historic claim information comprises at least one of clinical information, demographic information, and utilization information.

16. The method of claim 15, wherein the clinical information comprises at least one of hospitalizations, outpatient services, procedure codes, diagnostic codes, diagnostic-related group codes, drugs prescribed, chronic conditions, and an interval between encounters.

17. The method of claim 15, where in the demographic information comprises at least one of enrollee industry, employment status, sex, age, region of a country, an urban or rural setting, and relation to an insured person.

18. The method of claim 15, wherein the utilization information comprises one or both of historic cost and utilization trends.

19. A computer-implemented method for training a Bayesian belief network (BBN) model for evaluating enrollees of a health insurance plan, the method comprising:
   receiving, by a training module executed within a server, a first set of health insurance claim data for a first group of individuals from a client device over a network, the first group of individuals representing enrollees of one or more first health insurance plans and the first set of health insurance claim data representing historic insurance claim information for each individual in the first group of individuals, wherein the first set of historic insurance claim information includes co-morbid conditions;

separating, by the training module, the received first set of health insurance claim data into a training set of claim data and a holdout set of claim data;

creating, by the training module, a set of BBN model candidates, wherein creating the set of BBN model candidates comprises:

calculating distributions of discrete states for variables of the BBN network, and generating at least one of the following:
- a first BBN model by performing a preliminary modeling operation on the variables to identify appropriate machine learning parameters,
- a second BBN model by performing a global modeling operation to set the appropriate machine learning parameters and to observe variable relationships,
- a third BBN model by performing a naïve modeling operation to identify a contribution of each of the variables, or
- a fourth BBN model by performing a focused modeling operation on a subset of the variables identified in at least one of the preliminary modeling operation, the global modeling operation, and the naïve model operation, wherein the set of BBN model candidates comprises at least one of the first BBN model, the second BBN model, the third BBN model, or the fourth BBN model;

selecting a BBN model from the set of BBN model candidates which has the highest score among the set of BBN model candidates when evaluated using a predetermined scoring method, wherein the selected BBN model is a screening BBN model to identify individuals having risk characteristics associated with a disorder or a cost BBN model to produce cost estimates with and without intervention or treatment of the disorder;

validating the selected BBN model using the holdout set of claim data by generating a receiver operating characteristic (ROC) curve based on an outcome of the selected BBN model operated on the holdout set of claim data, and calculating an area under the curve (AUC) based on the ROC curve to evaluate predictive correctness of the selected BBN model given the holdout set of claim data;

generating a health insurance policy for one or more individuals using the validated BBN model; and transmitting the health insurance policy to a client device over a network.

20. The method of claim 1, wherein the insurance policy is further based on the cost estimates generated by the cost BBN model.

* * * * *